United States Patent [19]
Warden et al.

[11] Patent Number: 6,016,712
[45] Date of Patent: Jan. 25, 2000

[54] DEVICE FOR RECEIVING AND PROCESSING A SAMPLE

[75] Inventors: Laurence Warden, Poway; David E. Kaplan, Carlsbad, both of Calif.

[73] Assignee: Accumetrics, San Diego, Calif.

[21] Appl. No.: 08/933,443

[22] Filed: Sep. 18, 1997

[51] Int. Cl.[7] .................................................. G01L 3/02
[52] U.S. Cl. ................... 73/864.21; 73/864.22
[58] Field of Search ................. 73/864.21, 864.22, 73/864.35, 864.81, 863.83, 863.84; 422/73, 61, 68.1; 435/810; 436/66, 67

[56] References Cited

U.S. PATENT DOCUMENTS

| | | | |
|---|---|---|---|
| 4,749,658 | 6/1988 | Jaekel et al. | 436/180 |
| 4,786,394 | 11/1988 | Enzer et al. | 204/401 |
| 4,799,393 | 1/1989 | Uffenheimer | 73/864.22 |
| 4,868,129 | 9/1989 | Gibbons et al. | 436/179 |
| 4,946,795 | 8/1990 | Gibbons et al. | 436/179 |
| 5,077,017 | 12/1991 | Gorin et al. | 422/100 |
| 5,104,813 | 4/1992 | Besemer et al. | 436/179 |
| 5,316,730 | 5/1994 | Blake et al. | 422/73 |
| 5,447,440 | 9/1995 | Davis et al. | 435/6 |
| 5,500,187 | 3/1996 | Deoms et al. | 422/58 |
| 5,558,838 | 9/1996 | Uffenheimer | 73/864.22 |
| 5,591,403 | 1/1997 | Gavin et al. | 422/73 |
| 5,628,961 | 5/1997 | Davis et al. | 422/73 |
| 5,652,149 | 7/1997 | Mileaf et al. | 422/68.1 |

FOREIGN PATENT DOCUMENTS

WO 97/02357   1/1997   WIPO.

*Primary Examiner*—Robert Raevis
*Attorney, Agent, or Firm*—Heller Ehrman White & McAuliffe

[57] ABSTRACT

The present invention concerns devices for receiving and processing a sample. The device comprises a sample receiving element adapted to establish fluid communication with and receive a sample directly from a sample container. The sample receiving element also allows for introduction of a sample into the device. A first chamber is in fluid communication with the sample receiving element. One or more second chambers are in fluid communication with the first chamber. The device also comprises first and second ports. The first port provides for venting the device. The second port provides for establishing communication between the device and means for moving the sample from the sample receiving element to the first chamber and for moving the sample from the first chamber to the one or more second chambers. Also included as part of the device is means for controlling the precise amount of the sample introduced into each of the second chambers. The first chamber and/or one or more of the second chambers are adapted for processing the sample. Also disclosed are kits containing the above devices and methods of using the devices to process a sample.

21 Claims, 7 Drawing Sheets

ND RECEIVING AND
DEVICE FOR RECEIVING AND
PROCESSING A SAMPLE

BACKGROUND OF TEE INVENTION

1. Field of the Invention

This invention relates to the field of diagnostic assays and the collection and processing of samples therefor.

The ability to measure quantitatively a wide variety of physiologically active compounds, both naturally occurring and synthetic, has become of increasing importance, both as an adjunct to diagnosis and therapy. The medical industry has become increasingly dependent upon the ability to measure various entities in physiological fluids in order to be able to determine the health status of an individual, dosage level for drugs, use of illegal drugs, genomic sequences and the like. Thus, the capability of taking a physiological sample and rapidly analyzing for a particular component has made medical therapies more efficient and increasingly successful.

For the most part diagnostic assays of physiological fluids or biological samples for one or more analytes have required clinical laboratory determinations although there has been an increasing focus on being able to carry out assay determinations in the doctor's office and in the home. Numerous systems have been developed in efforts to try to address the various problems associated with analyses carried out in the clinical laboratory.

There is substantial interest in providing for protocols and devices which are simple, easy to manipulate, and reduce the opportunity for operator failure. The ideal situation would be collection of an unmeasured sample in a container, which is then sealed. Subsequently, the sample could then be introduced into an assay device without opening the sealed container and without the need for accurately measuring the sample. The device into which the sample is introduced provides for precise measurement of the sample to be analyzed, which is important in obtaining a quantitative result.

In may instances blood is a source of a sample to diagnose a patient's health or to monitor the efficacy of drugs that have been administered to the patient. Blood as a source for the determination of these parameters has many deficiencies when used directly or even when diluted with buffer. These deficiencies include: rapid coagulation, the presence of a large number of light absorbing and fluorescent substances, variations in composition, susceptibility to changes in relation to reagents used in assays, and variations In the presence or absence of oxygen. These properties complicate the use of blood as a sample for diagnostic purposes. Various techniques have been employed to avoid these problems, e.g., high dilution, addition of anticoagulants, separation of blood into plasma and its cellular components, and the like. During such manipulations great care must be taken to avoid lysis of red blood cells to avoid the release of hemoglobin, which can interfere with diagnostic assays. Despite the problems associated with the use of blood as the sample medium, in many instances, blood is the only source that provides the information of interest. Therefore, identifying ways of using whole blood, while diminishing the interference from its constituents is highly desirable. There is, therefore, substantial interest in devising new approaches for using and manipulating blood for diagnostic purposes.

Thus, the use of whole blood in diagnostic assays is not unusual in the medical field. When the volume of blood needed to perform the test becomes greater than a few drops, a blood collection container such as a vacuum tube or syringe is used. The subsequent delivery of the sample into the assay requires the transfer of blood from the collection container to an assay device. The transfer increases the risk of both hazardous contact to the clinician as well as alteration of the specimen. Also, in some circumstances, it is desirable to preprocess the blood sample such as by removal of cells from whole blood, lysing cells in whole blood, and so forth.

Certain devices are known for the collection of a sample for a qualitative determination of an analyte of interest. As may be appreciated, the considerations for collection of a sample for a quantitative determination of an analyte are much different. In general, for a qualitative result the collection of a precise amount of a sample is not a consideration.

One area of particular interest in analyses employing whole blood samples is the assessment of platelet function. The role of platelets in mammalian physiology is extraordinarily diverse, but their primary role is in promoting thrombus formation. In many situations, an evaluation of the ability of blood to clot is desired, a parameter that is frequently controlled by the ability of platelets to adhere and/or aggregate. Thus, one may wish to assess the adhesive functions of platelets. For example, one may wish to know whether to administer drugs that will block, or promote, clot formation, or one may need to detect deficiencies in platelet function prior to surgical procedures. In other instances one may be interested in evaluating the effectiveness of a platelet inhibitor that is being tested as a new drug or is being used as approved clinical treatment in a patient.

Platelets are known to aggregate under a variety of conditions and in the presence of a number of different reagents. Platelet aggregation is a term used to describe the binding of platelets to one another. The phenomenon can be induced by adding aggregation inducing agents to platelet rich plasma (PRP) or to whole blood. Platelet aggregation in vitro depends upon the ability of platelets to bind fibrinogen to their surfaces after activation by an aggregation inducing agent such as ADP or collagen.

Platelets play a critical role in the maintenance of normal homeostasis. When exposed to a damaged blood vessel, platelets will adhere to exposed sub endothelial matrix. Following the initial adhesion, various factors released at the site of injury such as thrombin, ADP and collagen activate the platelets. Once platelets are activated, a conformational change occurs in the platelet glycoprotein GPIIb/IIIa receptor allowing it to bind fibrinogen and/or von Willebrand factor.

It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

The success of aspirin, and more recently ticlopidine, in treating, and preventing ischemic complications of thrombosis has stimulated the search for more potent agents. New agents that block platelet GPIIb/IIIa receptors are being developed for use as antithrombotic agents, including peptides and peptidomimetics, based on the arginineglycineaspartic acid (RGD) and related cell recognition sequences. A recombinant murine/human chimeric antibody Fab fragment (c7E3Fab, abciximab, ReoPro™) c7E3 has been approved in Europe and the United States for use as adjunctive therapy in high risk angioplasty. Moreover, one additional trial (EPILOG), was stopped early by the Data and Safety Monitoring Boards because of the greater than expected benefit of 61% reduction in thrombotic events with c7E3 in the full range of patients undergoing coronary angioplasty. However, the benefit of GPIIb/IIIa blockers has been accompanied by an increased risk of bleeding. A number of other agents are currently in early and advanced trials, including agents that are orally active.

Intrinsic differences in pharmacokinetics and pharmacodynamics among the GPIIb/IIIa antagonists may affect the dose required to achieve a safe therapeutic antiplatelet effect. Beyond these overall differences in the drugs, however, interindividual variations in drug excretion and metabolism may have an impact on optimal drug dosing. Prolonged therapy, either with parenteral or oral agents, is likely to magnify the importance of interindividual differences, especially with pro drugs and low molecular weight agents that rely on renal excretion or hepatic metabolism.

Direct measurement of GPIIb/IIIa receptor blockade has been reported for only a few GPIIb/IIIa antagonists. An assay to measure GPIIb/IIIa receptor blockade by c7E3 Fab, based upon inhibition of platelet binding of radiolabelled c7E3 has been used to correlate GPIIb/IIIa receptor blockade, inhibition of platelet aggregation, prolongation of the bleeding time, and antithrombotic efficacy in animal models. Based on these results, the target level for coronary artery angioplasty was defined as >80% GPIIb/IIIa receptor blockade, and this level of blockade has proved efficacious in three separate Phase III studies in humans.

Available assays for evaluating GPIIb/IIIa receptor blockade, including platelet aggregation, bleeding time, thromboelastography, clot retraction, radiolabelled antibody binding, and flow cytometry are time consuming, require standardization, or require specialized equipment.

In vitro platelet aggregation is the laboratory method used to assess the in vivo ability of platelets to form the aggregates leading to a primary hemostatic plug. In this technique an aggregating agent such as ADP or collagen is added to whole blood or PRP and aggregation of platelets monitored. Platelet aggregometry is a diagnostic tool that can provide insights difficult to obtain by other techniques, thus aiding in patient diagnosis and selection of therapy. Current methods of monitoring platelet aggregation require expensive, laboratory dedicated instruments that are not easily portable and require standardization to ensure accurate quantitative results. In addition, unless performed using whole blood, results are unlikely to be available for several hours.

Currently there are two detection methods used in instruments with FDA clearance for performing platelet aggregometry: optical and impedance measurements. Optical detection of platelet aggregation is based on the observation that, as platelets aggregate into large clumps, there is an increase in light transmittance. Different aggregation-inducing agents stimulate different pathways of activation and different patterns of aggregation are observed. The main drawback of the optical method is that it must be performed on PRP, necessitating the separation of platelets from red blood cells and adjustment of the platelet count to a standardized value.

Impedance detection can be used to test anti coagulated blood with no need to isolate platelets from other components of the blood, although in many cases the sample is diluted before testing. The method detects aggregation by passing a very small electric current between two electrodes immersed in a sample of blood (or PRP) and measuring electrical impedance between the electrodes. During initial contact with the blood or PRP, the electrodes become coated with a monolayer of platelets. If no aggregating agent is added, no further interactions occur between the platelets and the electrodes and electrical impedance remains constant. When an aggregation inducing agent is added, platelets aggregate on the electrodes and there is an increase in impedance.

The CHRONO LOG Model 530 and Model 540 use the optical method for PRP and the impedance method for whole blood aggregometry. The impedance method has been shown to be substantially equivalent to the optical method for measuring platelet aggregation in PRP.

Various photometers are commercially available for measuring the light absorbance of liquid samples in microtitration plates or other sample holding vessels. Examples of such equipment are the MR 600 Microplate Reader (Dynatech Laboratories, Inc., Alexandria, Va.), and the Vmax Kinetic Microplate Reader (Molecular Devices, Palo Alto, Calif.).

It is desirable to have a rapid and simple platelet function assay including the ability to transfer blood to be tested from a collection container to an assay device without opening the collection container. In the setting of coronary angioplasty, it is desirable to have a platelet aggregation assay that could be conducted at the same time as the activated clotting time (ACT), which is performed to assess the adequacy of heparinization. During chronic infusions of GPIIb/IIIa antagonism, or with chronic oral therapy, periodic monitoring may also be desirable. In certain circumstances, as for example, prior to surgery or an invasive procedure, it may be desirable to rapidly determine whether the effect of the GPIIb/IIIa antagonist has worn off sufficiently to allow the surgery or procedure to be performed without further interventions to reverse the effect of the GPIIb/IIIa inhibitor. Finally, in the event of bleeding complications, a rapid measure of platelet function may be helpful in determining whether the bleeding is due to a high or toxic level of platelet inhibition. The level of platelet inhibition may also be helpful in guiding whether to reverse the drug effect with platelet transfusions or look for other causes of bleeding.

2. Previous Disclosures

O'Brien, J. R., Nature 202:1188 (1964) discloses aggregation studies of 2 mL plasma samples placed in a cuvette in an EEL titrometer or electrophotometer. Each sample is treated individually and aggregation is said to occur when the optical transmission increases.

Mills, D.C.B., and Roberts, G.C.K., J. Physiol. 193:443 453 (1967) disclose platelet aggregation measurements in a modified EEL Long Cell Absorptiometer (Evans Electroselenium Ltd., Halstead, Essex, U.K.). The measurements are taken on a 1 mL plasma sample, stirred from below by a magnetic stirrer while continuous recordings are made.

Michal, F., and Born, G.V.R., Nature New Biol. 231 220 (1971) disclose a modification of the traditional optical method of measuring aggregation which permits the simultaneous measurement of scattered and transmitted light. This method encompasses a modification of the cuvette chamber of an aggregometer to allow for the measurement of light scattered at right angles to the incident light beam. In the aggregometer the incident light illuminates a suspension of platelets which are kept in rapid motion by a magnet rotating in the bottom of the glass tube at 1,000 rpm. The sample volume is about 1 mL and the optical density is read individually for each sample which is kept in a water-jacketed environment at 37° C.

Fratontoni, et al., in U.S. Pat. No. 5,325,925 disclose the use of an agitated microtiter plate to assess aggregation in PRP.

Shaw, et al., in U.S. Pat. No. 5,427,913 disclose a method for determining platelet function in PRP by contacting the platelets in suspension with an immobilized extracellular matrix protein while applying mechanical stimulus to the platelets, and determining the platelet activation produced by various indicia.

Coagulation monitors are known for the analysis of whole blood. U.S. Pat. No. 3,695,842 describes a method of analyzing the transformation of a liquid, e.g. blood, to a gelatinous or solid mass. The coagulation system uses a vacutainer with all the necessary reagents, as well as a ferromagnetic component. Once the blood sample has been drawn into the vacutainer, it is placed into the instrument in an inclined manner. This procedure makes the ferromagnetic component sit at the bottom of the tube in close proximity to a magnetic reed switch. As the sample is rotated, gravity ensures that the component remains close to the reed switch. However, as the blood starts to clot, viscosity increases to the point where the component starts to rotate with the blood sample. The reed switch is thus activated, enabling a coagulation time to be estimated.

Hillman, et al., disclose a unit use cartridge in which dry reagents are placed into the analyzer which is then heated to 37° C. before a drop of brood is introduced. The sample is mixed with the reagent by capillary draw. The detection mechanism is based on laser light passing through the sample. Blood cells moving along the flow path yield a speckled pattern specific to unclotted blood. When the blood clots, movement ceases producing a pattern specific to clotted blood. Several patents disclose aspects of this technology and are described further below.

U.S. Pat. No. 4,756,884 discloses the component parts of the cartridge technology, which is based on capillary draw, including certain antibodies and reagents for blood clotting.

U.S. Pat. No. 4,948,961 discloses the components and method of use of an optical simulator cartridge used with the above instrument. U.S. Pat. No. 4,963,498 discloses a method of obtaining chemical information from the capillary draw cartridge. U.S. Pat. No. 5,004,923 discloses optical features by which the above instrument interrogates the cartridge Shenaq and Saleem, in "Effective Hemostasis in Cardiac Surgery," Eds: Ellison, N. and Jobes, D. R., Saunder & Co. (1988), utilize a sonic probe that is inserted into a cuvette containing the sample and reagents. The sonic probe responds to clot formation in the cuvette and, thus, can be used to measure the coagulation time.

PCT application WO 89/06803 describes a unit use cartridge having two capillary tubes that simultaneously draw blood from a single finger stick. The design allows for duplicate measurement or two different measurements based on different reagent coatings. Blood coagulation is measured by charges in light permeability through the capillary tube.

U.S. Pat. No. 5,110,727 describes another format based on the use of magnetic particles mixed into a dry reagent contained within a flat capillary chamber. An applied oscillating magnetic field from the instrument causes the particles to oscillate once the reagent has dissolved in the blood. This motion is monitored optically. When the blood clots, the particles become entrapped and motion is diminished. Fibrinolysis assays are performed by monitoring the reverse process (See, Oberhardt, et al., Clin. Chem. (1992) 37:520).

Machado, et al., J. Acoust. Soc. Am (1991) 90:1749 describe another method of detecting coagulation based on ultrasonic scattering from 200 micron glass spheres suspended in a blood sample. Amplitude and phase changes of the scattered waves are used to detect coagulation.

Varon, et al., in U.S. Pat. No. 5,523,238, describe a method for determining platelet function by introducing a blood sample into a vessel having a flat bottom, the inner surface of which is covered with a substrate capable of inducing platelet adhesion thereto and aggregation; rotating the preparation inside the vessel, inducing shear forces at the surface which aggregate the platelets; and determining parameters of the adhered blood platelets, such as number of adhered platelets, aggregate size, aggregate morphology, total area covered by the aggregates, and distribution of adhered platelets or aggregates on the surface.

Coller, in pending U.S. patent applications Ser. Nos. 08/315,026 and 08/754,773, describes a method for the analysis of whole blood for GPIIb/IIIa receptor activity. The disclosed method relies upon the visual observation of platelet mediated agglutination of fibrinogen coated beads.

The disclosure of all the aforementioned patents and publications is incorporated herein by reference.

SUMMARY OF THE INVENTION

One aspect of the invention concerns a device for receiving and processing a sample. The device comprises a sample receiving element adapted to establish fluid communication with and receive a sample directly from a sample container. The sample receiving element also allows for introduction of a sample into the device. A first chamber is in fluid communication with the sample receiving element. One or more second chambers are in fluid communication with the first chamber. The device also comprises first and second ports. The first port provides for venting the device. The second port provides for establishing communication between the device and means for moving the sample from the sample receiving element to the first chamber and for moving the sample from the first chamber to the one or more second chambers. The device may also include means for controlling the precise amount of the sample introduced into each of the second chambers. The first chamber and/or one or more of the second chambers are adapted for processing the sample.

Another embodiment of the present invention also concerns a device for receiving and processing a sample. In this embodiment a sample receiving element has an input port that provides for direct sealing connection and establishment of fluid communication with a sample container such that sample in the container is capable of introduction into the device. A first chamber is in fluid communication with the input port. One or more second chambers are each respectively in fluid communication with the first chamber. The second chambers contain one or more reagents for processing the sample. The device has first and second ports. The first port provides for connecting the device with a pressure varying apparatus for alternately increasing and decreasing pressure in the device. The second port provides for venting the device. The device also includes means for permitting air to escape from the one or more second chambers and for sealing the one or more second chambers when a predetermined amount of the sample fills the one or more second chambers.

Another embodiment of a device in accordance with the present invention has an input port comprising a needle for piercing a sample container and allowing introduction of a sample suspected of containing an analyte directly into the device. A first chamber is in fluid communication with the input port by means of a first channel connecting the input port and the first chamber. A manifold is in fluid communication with the first chamber. One or more second chambers are each respectively in fluid communication with the manifold by means of a second channel between the manifold and the respective second chamber. One or more of the second chambers contain one or more reagents for conducting an assay. A first port is included for connecting the device with a pressure varying apparatus for alternately increasing and decreasing pressure in the device. The device also includes a second port for venting the device. The device further comprises a vent plug for each of the one or more second chambers for permitting air to vent from the one or more second chambers and sealing the one or more second chambers when the sample reaches the vent plug.

Another embodiment of the present invention is a kit for processing a sample. The kit comprises in packaged combination a device as described above and reagents for processing the sample other than reagents that are included in the device itself.

Another embodiment of the present invention is a method for receiving and processing a sample. In the method a sample is applied to a sample receiving element of a device as described above. The first port is connected to a pressure varying apparatus. Pressure in the device is adjusted to cause the sample to flow from the sample receiving element to the first chamber. After a holding period pressure is again adjusted in the device to cause the sample to flow from the first chamber to the one or more of the second chambers where the sample is processed.

DETAILED DESCRIPTION OF THE INVENTION

Figure 1:
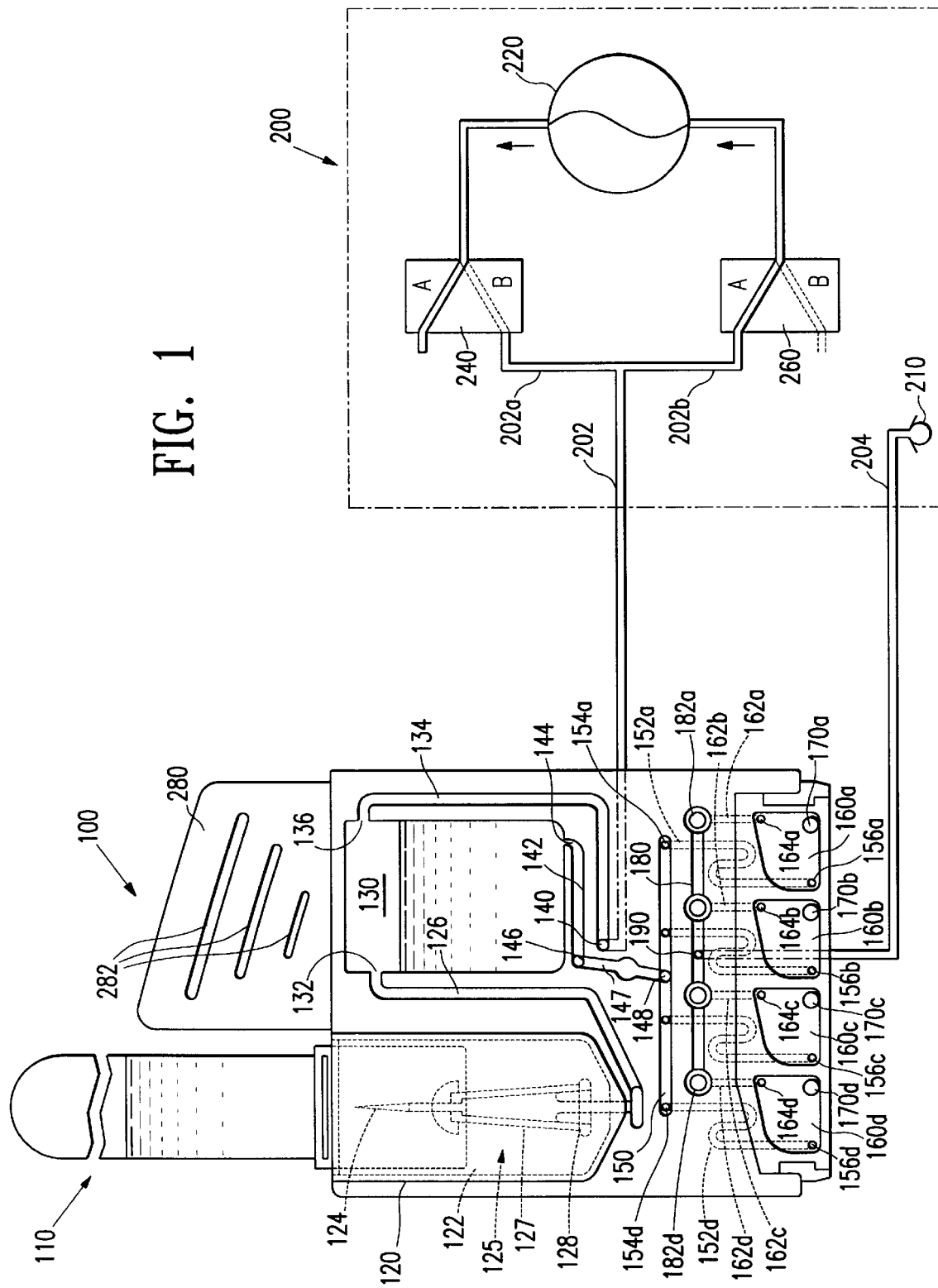
FIG. 1 is a diagrammatic plan view of a device according to the subject invention.

The present invention provides for the collection in a sealed container of a sample to be analyzed and transferring the sample into a device that can be used in conjunction with an assay apparatus for analysis of the sample and can then be easily disposed of if desired. The transfer can be accomplished without opening the sealed container, thus avoiding exposing the clinician to undue risks and avoiding placing the blood in an environment that may be detrimental to its ability to function as a reliable source for a determination of an analyte. The device permits the measuring of precise amounts of the sample into chambers for analysis. The sample can be conditioned with reagents and analyzed in the device of the present invention, which can be disposable.

Before proceeding further with a detailed description of the present invention, a number of terms as used herein are defined.

Sample—any solution, synthetic or natural, containing an analyte, including body fluids such as, for example, whole blood, blood fractions such as serum and plasma, synovial fluid, cerebro-spinal fluid, amniotic fluid, semen, cervical mucus, sputum, saliva, gingival fluid, urine, and the like, and aqueous or water soluble solutions of natural or synthetic compounds, particularly, compounds that are potential therapeutic drugs, and it is desired to determine if the compound binds to a specific receptor. The amount of the sample depends on the nature of the sample and the analyte contained therein. For fluid samples such as whole blood, saliva, urine and the like the amount of the sample is usually about 0.1 to 10 ml, more usually, about 1.8 to 4.5 ml. The term "sample" includes unprocessed samples directly from a patient or samples that have been pretreated and prepared in any convenient medium although an aqueous medium is preferred.

As mentioned above, the sample may be preprocessed prior to placing the sample in a sample container. Such preprocessing may include lysing of cells in the sample, releasing an analyte from binding materials in a sample, absorbing unwanted materials by affinity matrices, and so forth. Reagents for lysing cells in the sample include, for example, ammonium chloride, sodium chloride, detergents such as Triton X-100, Zwittergen and the like. The amount of the lysing reagent applied to the sample is generally sufficient to bring about the level of lysing desired and is usually about 0.01 to 10% by weight.

Other preprocessing reagents include precipitation reagents, affinity matrices with antibodies or antigens or lectins and so forth. The amount of such a reagent employed is generally sufficient to achieve the desired result and the reagent is applied in a manner similar to that described above for the stabilization reagent.

Analyte—the substance to be determined. The analyte may be any chemical entity and includes ligands and receptors, where the ligand and the receptor are defined as members of a specific binding pair that have an affinity or avidity for each other. The ligand may be a hapten or antigen, where haptens generally range from about 100 to 5000 molecular weight and include drugs of abuse such as cocaine, marijuana, etc., and therapeutic drugs such as cyclosporin, theophylline, dilantia, antibiotics such as amikacin, tobramycin, anticonvulsants, etc., and the like. Antigens generally range from about 2500 molecular weight to any upper limit such as, e.g., one million or more, and include cancer antigens such as PSA, CEA, AFP, CA19.9, etc., cardiac markers such as myoglobin, CKMB, etc., and so forth. Analytes may include naturally occurring ligands and receptors, synthetic compounds, pollutants, contaminants, microorganisms, e.g., viruses such as HIV virus, herpes virus (HSV) and the like, unicellular organisms, etc., blood components such as platelets, and the like and receptors thereon, blood proteins such as hemoglobin Alc, HLA, and the like, surface membrane proteins, cytokines, interferons, hormones, growth factors, etc. Receptors may be naturally occurring or synthetic, for the most part being proteins, such as immunoglobulins, fragments thereof, particularly monovalent fragments of immunoglobulins, e.g., Fab, Fv, etc., enzymes, naturally occurring receptors, e.g., T-cell receptors, hormone receptors, surface membrane receptors, lectins, etc. Other specific binding pairs include nucleic acids, e.g., DNA and RNA. For disclosure of certain specific ligands and receptors, see U.S. Pat. No. 3,996,345, columns 10–17, which disclosure is incorporated herein by reference. Analyte specific assays have been used to detect antibodies produced in response to infection, components of pathogenic agents, levels of drugs, hormones, and enzymes, etc. In addition to medicine, immunoassays and other related assays have also found numerous applications in manufacturing industries, for example, the detection of food contaminants.

Specific binding—the specific recognition of one of two different molecules for the other compared to substantially less recognition of other molecules.

Specific binding molecule—one of two different molecules having an area on the surface or in a cavity that specifically binds to, and is thereby defined as, complementary with a particular spatial and polar organization of the other molecule. The members of the specific binding pair may be an antibody and antigen, antibody and hapten, ligand and receptor, and so forth.

Receptor—that part of a molecule capable of recognizing and binding to an epitope.

Ligand—a molecule having an epitope to which a receptor can bind; a receptor may be a ligand for another receptor.

Label or reporter molecule—a chemical entity capable of being detected by a suitable detection means, including, but not limited to, spectrophotometric, chemiluminescent, immunochemical, or radiochemical means. The reporter molecule can be conjugated to another molecule such as a ligand or an antibody by procedures well-known in the art. Typically, the reporter molecule contains a functional group suitable for attachment to the ligand or antibody. The functional groups suitable for attaching the reporter group are usually activated esters or alkylating agents. Details of techniques for attaching reporter groups are well known in the art. See, for example, Matthews, et al., Anal. Biochem. (1985) 151:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like.

As mentioned above, the reporter molecule is a member of a signal producing system, which may have one or more components, at least one of which is the reporter molecule. The signal producing system includes all of the reagents required to produce a measurable signal. Other components of the signal producing system can include substrates, coenzymes, enhancers, activators, chemiluminescent compounds, cofactors, inhibitors, scavengers, specific binding substances, and the like.

As mentioned above, the present device is used for collecting a sample to be analyzed in a sealed container and transferring such sample into an assay device that can be used in conjunction with an assay apparatus for analysis of the sample. The transfer of sample into the present device is carried out without opening the sealed container. The present device also provides for the measuring of precise amounts of the sample into chambers for analysis.

One aspect of the invention concerns a device for receiving and processing a sample. The device comprises a sample receiving element adapted to establish fluid communication with and receive a sample directly from a sample container. The sample container is usually a container in which the sample to be processed is collected. The sample container may be in any form such as a syringe, test tube, cuvette, vial, cartridge and the like. For blood samples the sample container may conveniently be a Vacutainer® container, a syringe and so forth. Suitable materials for fabrication of the sample container are glass, plastic and the like. In general, any material may be used that does not react with, or otherwise cause detrimental effects on, the sample or any solvents in which the sample is dissolved or suspended. The sample container may not necessarily be a container in which sample is collected. For example, the sample container may be a container in which a sample is placed after collection and pre-processing such as to remove debris, filter cells, add diluents and so forth.

An appropriate element is included as part of the sample container for attachment to the sample receiving element of a device in accordance with the present invention. For instance, if the sample receiving element of the present device includes a needle or other piercing element, the sample container comprises a corresponding element capable of being pierced such as a septum, membrane, and the like. Alternatively, the sample receiving element and the sample container can have other mating elements that provide for sealed fluid communication between the instant device and the sample container. For example, the sample container may include a piercing element and the sample receiving element may comprise a corresponding septum. The primary principle involved is that sample can be transferred from the sample container to the present device without opening the sample container. Other suitable mating elements include luer fittings and other mechanical sealing connections.

The sample container may include one or more other features depending on the nature of the sample and its processing. For example, separation elements such as filters, membranes and the like may be included. As mentioned above, in addition to establishing fluid communication between the sample container and the present device, the sample receiving element also allows for introduction of a sample into the device. A filter element may be employed for removing particles and other debris from the sample. In one embodiment, where it desired to analyze serum or plasma, the filter element can provide for the efficient removal of red blood cells from a whole blood sample so as to provide a serum or plasma sample substantially free of interfering red blood cells or hemoglobin or metabolic or degradation products thereof. The filter element can also be used to remove particles and other unwanted materials from other types of samples, such as urine and the like.

The sample receiving element may be of any suitable design, preferably a design that provides for holding the sample container when the latter is secured to the instant device. Conveniently, the sample receiving element may be a recess, such as a well or the like, in a housing. In such a configuration part or all of the sample container can be secured in the well. The recess may include friction elements for securing the sample container in the well. The friction elements may take the form of circumferential ribs, longitudinal ribs, spring fingers and so forth. As described above, the sample receiving element also comprises a component for establishing sealed fluid communication with the sample container.

One convenient design for the sample receiving element is a needle assembly comprising a needle and a needle holding means that is attached to the base of the bottom inside wall of a well. The needle holding means generally comprises a cylindrical passageway in a housing in which the needle can be mounted. The device may be manufactured with the needle secured in the housing. On the other hand, the needle can be secured in the housing prior to use. The needle is usually constructed from metal tubing and is usually about 26 to 16 gage. The dimensions of the needle are about 10 to 15 mm, preferably, about 13 mm in length and about 1 to 1.5 mm, preferably, about 1.3 mm, in outside diameter, and about 0.5 to 1 mm, preferably, about 0.75 mm, in inside diameter. The needle holding means can be of any convenient size and shape as long as it holds the needle to permit ready piercing of the sample container. The needle holding means generally has a bore therethrough to provide access of the sample to the device. The needle assembly may include a cover for the needle portion to protect both the needle and the user.

At least one first chamber is in fluid communication with the sample receiving element. Fluid communication may occur through a channel or capillary between the sample receiving element and the first chamber. Generally, the size of the channel or capillary is about 0.1 mm to about 3 mm, more usually, 0.8 to 1.3 mm, in diameter. The size of the first chamber is dependent on the nature of the sample, the suspected concentration of any analyte to be determined, sample heating time and so forth. Generally, the first chamber is about 0.1 to 5 ml, usually about 0.6 to about 2 ml.

The first chamber serves as a staging area for the sample to be processed. In the first chamber the sample may be processed such as by incubation at a particular temperature or temperatures, exposure to certain processing agents such as, e.g., enzymes, reagents, activators, inhibitors, lysing agents contained in the first chamber, and so forth. It is desirable that the communication between the sample receiving element and the first chamber occur at a point, the fill point, in the first chamber that provides maximum separation between the sample input point into the first chamber and the point at which pressure is adjusted in the first chamber. Furthermore, preferably, the fill point is also remote from the point at which fluid exits the first chamber (exit point). In a preferred embodiment the fill point is at or near the top portion of the first chamber and the exit point is at or near the bottom of the first chamber. Such a configuration maximizes the avoidance of premature filling of the first chamber. Also included is means for preventing premature movement of fluid out of the first chamber. Exemplary of such means are valves either passive or active by external means, resistive elements, capillary stop junctions, and the like.

The device also includes one or more second chambers that are in fluid communication with the first chamber. Fluid communication may occur through a channel or capillary between each of the second chambers and the first chamber. Generally, the size of the channel or capillary is about 0.1 mm to about 3 mm, more usually, 0.8 to 1.3 mm, in diameter. Generally, the first chamber is about 0.1 to 5 ml, usually about 0.6 to about 2 ml.

A detector can be included between the first chamber and the second chambers to monitor movement of the sample into the second chambers prior to the desired time. Premature filling of the second chambers can be detected in this fashion. The detector may take the form of a transmissive or reflective optical sensor, ultrasonic detector and the like. This may also be used as means for accurate measurement of the start time to fill.

The second chambers are used for conducting further processing of the sample. For example, the second chambers can contain various reagents for conducting an assay. A mixing means may be included in the second chambers for mixing the reagents with the sample introduced into the second chambers. A suitable mixing means is a mixing ball or the like. The mixing ball may be made from material susceptible to magnetic influence, such as ferrous material and the like, and caused to move at an appropriate time by application of a magnetic field. In a preferred embodiment the second chambers are constructed so that the results of an assay may be read either visually or mechanically. Accordingly, the second chambers are usually optically transmissive so that signals generated in an assay may be read, for example, when the present device is inserted into an appropriate instrument.

The device also comprises first and second ports. The first port provides for venting the device. The port can be adapted so that it readily connects to a valve for controlling the outlet of air or other gas from the device. In general, the valve permits flow only in one direction. Suitable valves include check valves, solenoid valves, shuttle valves and so forth. Usually, the first port is adapted for ready connection to a valve by mating means such as a compliant fitting, luer style fitting and the like. The corresponding mating means from the venting valve is generally found at the end of a channel, capillary, or other tubing. The venting valve and its capillary may be part of an apparatus or instrument in which the present device is inserted.

The second port provides for establishing communication between the device and means for moving the sample from the sample receiving element to the first chamber and for moving the sample from the first chamber to the one or more second chambers. One such means is alternately increasing and decreasing pressure in the device. In one embodiment such means comprises a capillary or channel that is branched and forms a loop at one end, thus creating a pneumatic circuit. The second port is at the end of a channel or capillary leading from the first chamber, preferably, from a point adjacent the top of the first chamber and opposite the fill point to provide optimum filling of the first chamber and transfer to the second chambers at an appropriate point in time. Included within the loop are two-three way valves separated by an intervening air pump, which may be, for example, a diaphragm pump, piston, rotary vane pump and the like. If a reversible pump is used, only one two-way valve is required. The valves are connected to the air pump and to the capillary and are configured such that in one position air may be pumped into the device to create pressure and in another position air may be pumped out of the device to create a vacuum. The pneumatic circuit conveniently may be part of an apparatus in which the present device is inserted. Usually, the second port is adapted for ready connection to the capillary from the pneumatic circuit by mating means such as compliant coupling, luer style fitting and so forth. The corresponding mating means from the pneumatic circuit is generally found at the end of a channel, capillary, or other tubing.

When the present device comprises more than one second chamber, the channel leading from the first chamber to the second chambers is interrupted by a first manifold. The position of the manifold is generally after the detector mentioned above, if such is included in the device. The size of the manifold is dependent upon the volume of the sample to be moved to the second chambers. Usually, the first manifold is about 0.1 to about 3 mm, in diameter, more usually, 0.8 to 1.3 mm. The cross-sectional area of the first manifold may be varied to maintain proper flow characteristics.

Each of the second chambers is connected to the first manifold by a channel or capillary, which connects to the second chamber, preferably, at a point adjacent the bottom of the second chamber. This channel or capillary is configured to prevent any reagents or other materials in the second chambers from contaminating the common areas of the device, particularly, the first manifold mentioned above. To this end, the channels or capillaries may have an S- shape so as to form a J-trap to prevent migration of reagent.

Generally, the size of the channels or capillaries is about 0.1 to about 3 mm, more usually, 0.5 to 1 mm, in diameter.

Each of the second chambers is in fluid communication with an exit port that is part of a second manifold. Usually, each second chamber is connected to its respective exit port by means of a channel or capillary. Generally, the size of the channel or capillary is about 0.1 to about 2 mm, more usually, 0.3 to 0.7 mm, in diameter. One end of the channel or capillary is usually connected adjacent to the top of the second chamber.

Also included as part of the device is means for controlling the precise amount of the sample introduced into each of the second chambers. In one embodiment this is achieved by having the point of connection for the channel or capillary connected to the exit port configured with respect to the fill point so that all air within the second chamber is forced out through the exit port. Optimally, such a configuration is achieved by positioning the point of connection diagonally opposed to the fill point. Furthermore, the shape of the second chamber may be chosen to optimize removal of air during filling and controlling the precise amount of sample introduced into the second chambers. To this end, the shape of the second chamber can be selected so that the top of the second chamber slopes upwardly to the point of connection of the channel or capillary leading to the second manifold. The shape of the second chambers, therefore, may be rhomboidal, triangular and the like. In this way precise filling of the second chambers can be realized, which is important for obtaining accurate, reproducible quantitative results in assays.

Each exit port allows air to escape from the second chamber as the chamber fills with sample. The exit port is designed to permit air, but not liquid, to escape from the second chamber. This effect may be achieved in a number of ways. For example, the exit port may be fitted with a material that permits air to pass through but, when liquid contacts the material, a seal is formed. Such materials include, by way of illustration and not limitation, porous polymer, e.g., Porex XM-1374® (from Porex Technologies, Inc., hydrophobic membranes such as, e.g., Gore-Tex™ (from W.L. Gore & Associates, Inc.), and the like. Typically, the size of the exit ports is about 0.1 to 0.2 mm, usually about 0.3 to about 0.7 mm. Other means for achieving the above effect include solenoid valves and optical sensors to close off ports. The exit port may also include a detector for detecting when the second chambers are filled. Such detectors include, for example, reflective and transmissive optical detectors, ultrasonic detectors and the like.

An embodiment of a device in accordance with the present invention is depicted in FIG. 1 by way of illustration and not limitation. Device 100 is shown with a sample container 110 mated with a sample receiving element 120, which comprises well 122. An input needle 124 is part of a needle assembly 125, which comprises needle 124, needle holder 127 and base 128 affixed to the bottom inside wall of well 122. Both needle holder 127 and base 128 comprise a longitudinal bore to provide for fluid to enter device 100. Needle 124 is in fluid communication with a first chamber 130 by means of a first channel 126, which at one end is connected to base 128 of needle assembly 125 and at the other end to an upper part 132 of first chamber 130.

A second channel 134 is connected at one end 136 to first chamber 130 and terminates at the other end at port 140. A third channel 142 provides fluid communication between first chamber 130 and first manifold 150. Accordingly, 142 is connected at its one end 144 to the base of 130 and at its other end 146 to indicator 147. The purpose of indicator 147 is to monitor flow out of first chamber 130 so that premature leakage of fluid from first chamber 130 may be detected. Indicator 147 is connected at point 148 to first manifold 150, thus lying between first manifold 150 and third channel 142 and forming part of the fluid communication between first chamber 130 and first manifold 150.

Fourth channels 152 (152a, 152b, 152c and 152d) provide fluid communication between first manifold 150 and second chambers 160. The device depicted has second chambers 160a, 160b, 160c and 160d. Lying within second chambers 160 are mixing balls 170 (170a, 170b, 170c and 170d, respectively). Fourth channels 152 connect at one end 154 (154a, 154b, 154c and 154d, respectively) to first manifold 150 and at the other end 156 (156a, 156b, 156c and 156d, respectively) to the bottom left of second chambers 160. Diagonally across from 156 are fifth channels 162 connected at one end 164 to the top right corner of 160 and at the other end to second manifold 180 at vent plugs 182 (182a, 182b, 182c and 182d, respectively). Second manifold 180 contains vent port 190.

Device 100 depicted in FIG. 1 is shown in conjunction with pneumatic circuit 200 wherein communication is established between device 100 and pneumatic circuit 200. To achieve such communication, port 140 is connected to sixth channel 202 and vent port 190 is connected to seventh channel 204, which terminates at check valve 210. Sixth channel 202 provides for fluid communication between port 140 and pump 220. Sixth channel 202 branches to give 202a and 202b. Three way valve 240 lies between 202 and pump 220 along 202a and three way valve 260 lies between 202 and pump 220 along 202b. The three-way valves 240 and 260 each have positions A and B. When valves 240 and 260 are in position A, valve 240 is open to the atmosphere and valve 260 is on line with channel 202. Conversely, when valves 240 and 260 are in position B, valve 260 is open to the atmosphere and valve 240 is on line with channel 202.

The device depicted in FIG. 1 also includes holder panel 280 for gripping the device. Holder panel 280 has slots 282, which provide a firmer gripping means as the device is manipulated to secure sample container 110 and to place device 100 in a suitable instrument for connection to a pressure varying apparatus and/or to read the results of an assay.

As mentioned above, the device of this invention is generally useful for the analysis of fluid samples, particularly of physiological fluid samples.

In the embodiment of FIG. 1, a sample in removable sample container 110 (not a part of the invention) is inverted and mounted in well 122 of sample receiving element 120. The top of the sample container has a septum, which is pierced by needle assembly 124 so that fluid may flow into device 100. To induce flow of sample into the device, negative pressure is applied to first chamber 130 via i port 140, which is shown attached to exemplary pneumatic circuit 200. As mentioned above, pneumatic circuit 200 comprises an air pump 220 and two three way valves 240 and 260. In use, the valves 240 and 260 are set at positions A to remove air from the first chamber 130 and draw sample into first chamber 130. Sample is then transferred to second chambers 160 by applying positive pressure to first chamber 130 through port 140. This is accomplished by switching the three way valves 240 and 260 to position B. Fluid enters second chambers 160 via first manifold 150. Second chambers 160 optionally contain reagents and mixing balls 170. Fluid fills each of second chambers 160 up to vent plugs 180.

Vent plugs 180 permit passage of air but not of liquid. Air passes through vent port 190 and out check valve 210.

The device may be fabricated from individual injection molded parts or by any other convenient process. The device may be fabricated from a material that is not reactive with the sample to be analyzed or the processing reagents employed. Furthermore, the material must be able to withstand the temperatures employed in a processing of the sample. In general, any material may be used that does not react with, or otherwise cause detrimental effects on, the sample or any solvents in which the sample is dissolved or suspended. Suitable materials for the manufacture of the present device include, for example, polystyrene, acrylonitrile-butadiene-styrene (ABS), styrene-acrylonitrile (SAN), polyethylene terephthalate (PET), polycarbonate and so forth.

Figure 2:
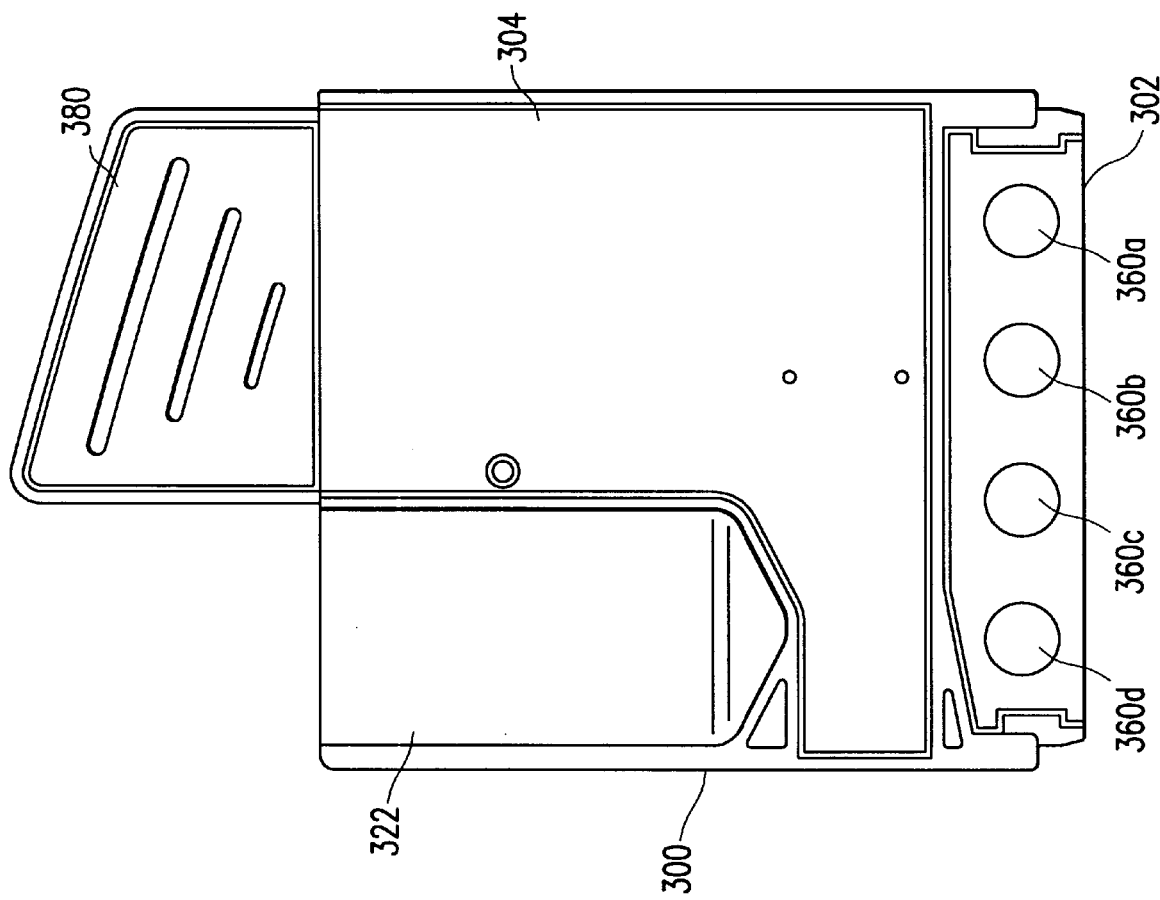
FIG. 2 is a plan view of an assembled device of FIG. 1.
Figure 3:
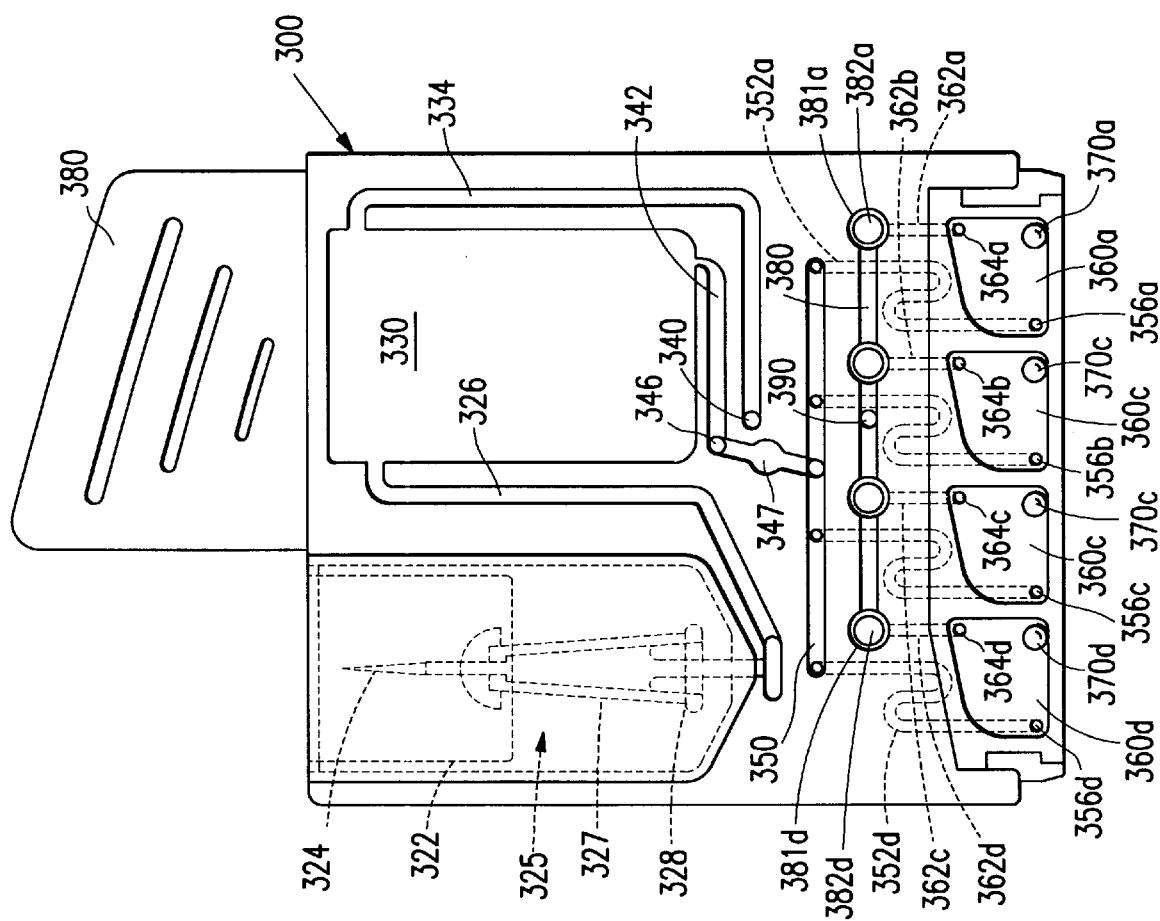
FIG. 3 is a diagrammatic plan view of the device of FIG. 2 without a cover plate.
Figure 4:
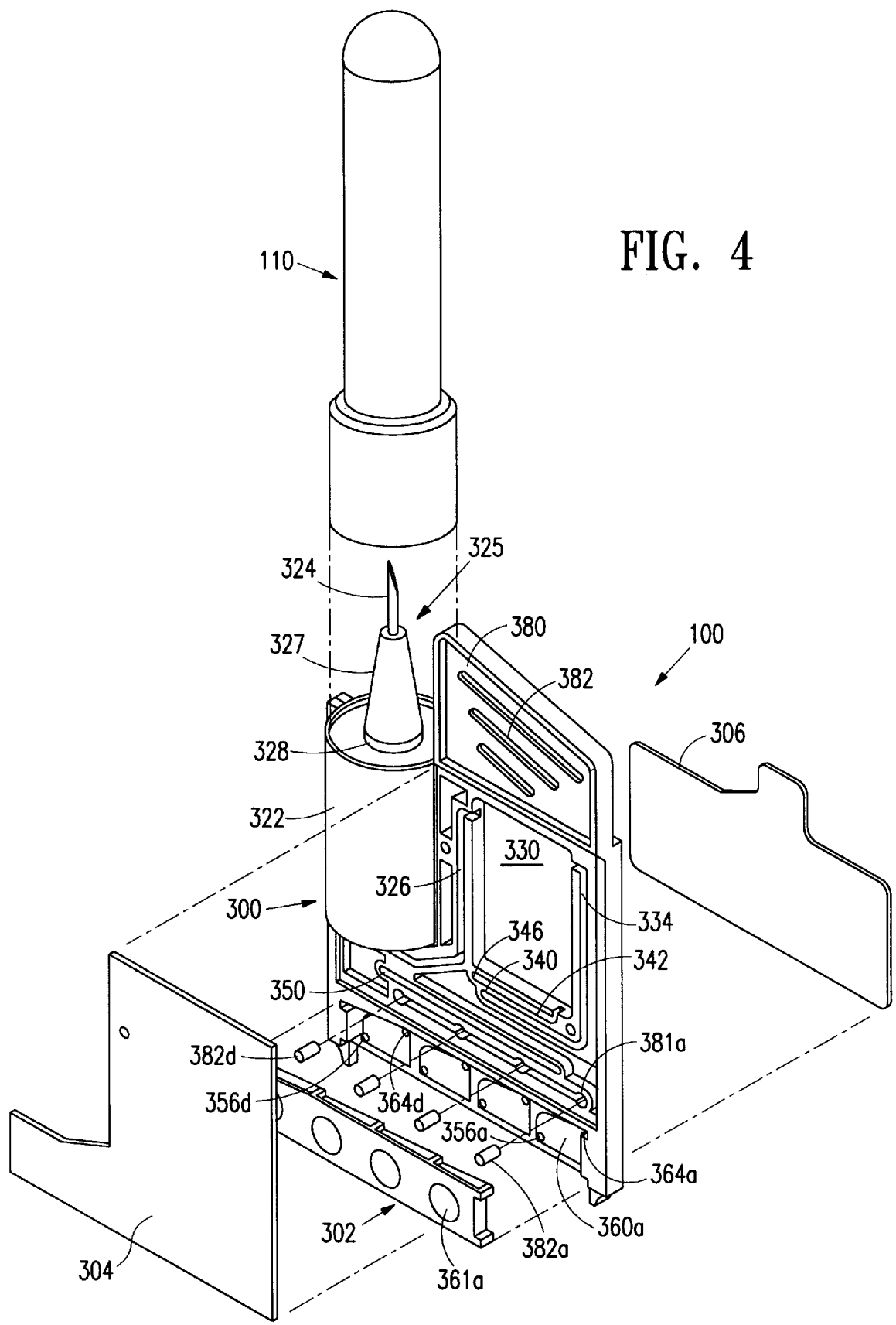
FIG. 4 is an exploded view of the device of FIG. 1.

For further understanding of fabrication of a device in accordance with the present invention, by way of example and not limitation, reference is made to FIGS. 2–4. The device depicted is that shown in FIG. 1. There are four individual parts for this embodiment of the present device, namely, housing assembly plate 300, second chamber assembly plate 302, cover plate 304 and rear plate 306. Housing assembly plate 300 includes well 322, which is preformed in housing assembly plate 300. Also preformed in the bottom of well 322 is base 328 and needle holder 327, which are part of needle assembly 325. Needle 324 may be secured in needle holder 327. First channel 326, first chamber 330, second channel 334 including first port 340, third channel 342, indicator 347, first manifold 350, fourth channels 352 (352a, 352b, 352c and 352d), fifth channels 362 (362a, 362b, 362c and 362d), second manifold 380, vent port 390, and vent plug recesses 381 (381a, 381b, 381c and 381d) are all included in housing plate 300. Vent plugs 382 (382a, 382b, 382c and 382d) are placed in vent plug recesses 381. Second chamber plate 302 comprises a cover for second chambers 360 (360a, 360b, 360c and 360d). Second chambers 360 having appropriate openings for aligning with fourth channels 352 at ends 356 (356a, 356b, 356c and 356d). Second chamber plate 302 has appropriate openings for aligning with fifth channels 362 at ends 364 (364a, 364b; 364c and 364d). Housing plate 300 includes a recessed area for inserting second chamber plate 302, which is placed in device 300 so that the openings in the second chambers align with ends 356 and 364. Mixing balls 370 are placed in the second chambers of second chamber plate 302 prior to welding to housing plate 300. Plate 302 is then welded to secure it to housing plate 300. Finally, cover plate 304 and rear plate 306 are welded into position on housing plate 300, thereby completing the manufacture of the device 100.

The primary factor in determining the size of the device is the ease of use of such device. The device should not be so large or so small as to be cumbersome or difficult to use. Furthermore, the size of the device should be such that it is easily manipulated to insert the sample container and to insert the device into an apparatus that has the aforementioned pneumatic circuit as well as a reading means for determining the result of an assay.

Figure 5:
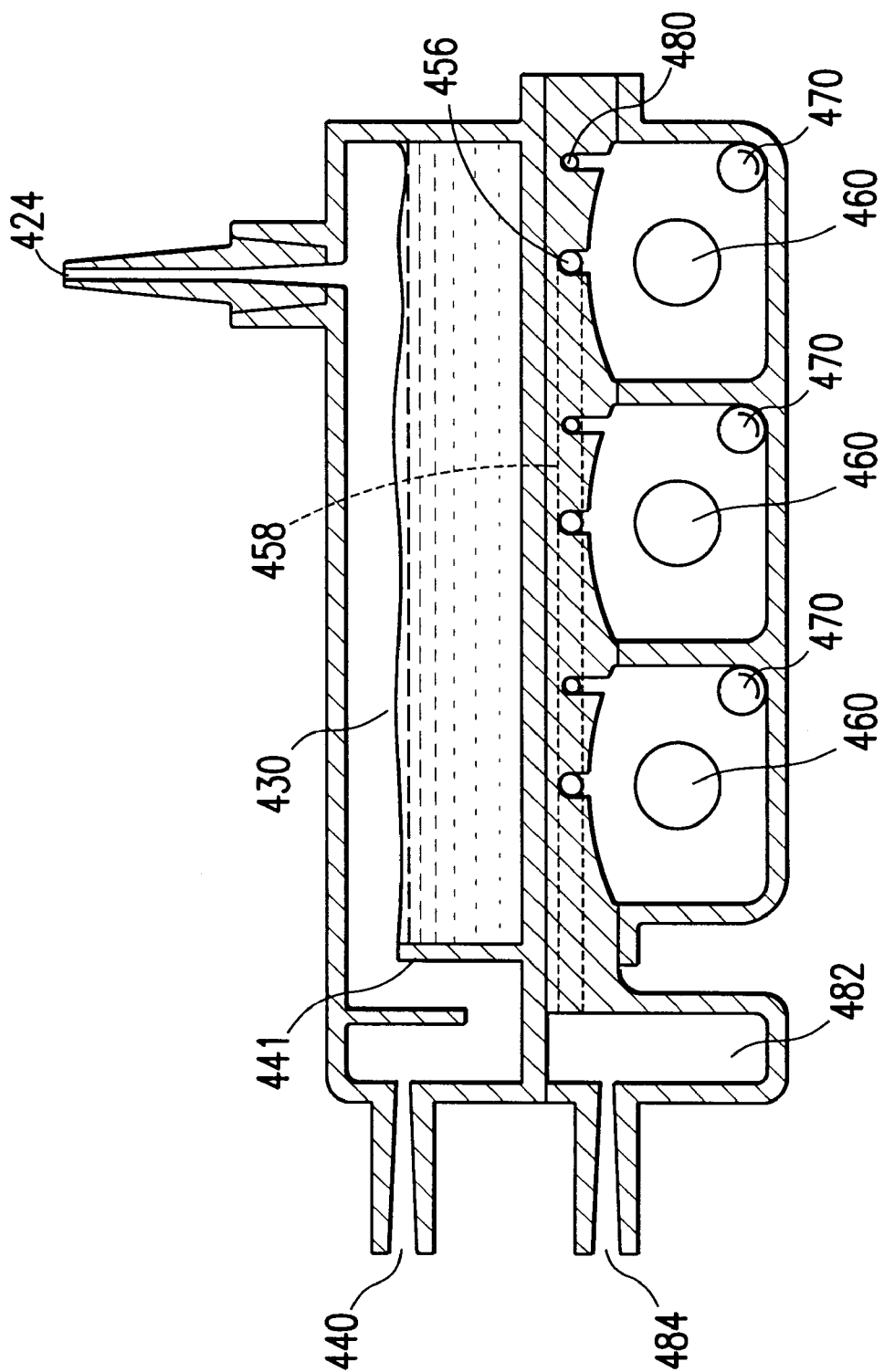
FIG. 5 is diagrammatic plan view of an alternative embodiment of a device in accordance with the present invention.

Another embodiment of a device in accordance with the present invention is depicted in FIG. 5. In the device of FIG. 5 fluid is drawn through sample inlet port 424 into first chamber 430 via application of vacuum at port 440. Dam 441 prevents direct flow into the vacuum port 440. The application of positive pressure to port 440 forces fluid into second chambers 460, with mixing balls 470, through fill ports 480, which are in fluid communication with first chamber 430 by means of a manifold (not shown. Vent plugs 456 prevent overflow of fluid while permitting passage of air. Overflow well 482 is connected to check valve connection 484 and to vent plugs 456 by means of manifold 458.

As mentioned above, the device may include one or more reagents for processing the sample. The nature of the reagents for processing the sample will depend on the type of processing to be carried out. Such processing reagents may include reagents for stabilizing and/or preserving the sample or the analyte contained therein and may be included in the first chamber. If the sample is to be subjected to an assay, the nature of the reagents depends on the nature of the assay to be conducted. For example, if the sample is to be analyzed by conducting an immunoassay, the second chamber may include an antibody reagent.

The reagents for processing a sample may include one or more stabilization reagents and/or preservatives for stabilizing and preserving the sample and/or the analyte, applied to the device. Examples of stabilization reagents are chelating compounds such as ethylenediaminetetraacetic acid, water soluble polymers such as polyethylene glycol, polyvinyl pyrrolidine, polyvinyl alcohol, and the like, protease inhibitors such as aprotinin, phenyl methyl sulfonyl fluoride (PMSF), and the like. The amount of stabilization reagent employed is, in general, that which would be effective in bringing about the desired stabilization. The stabilization reagent may be present in an amount of about 0.01 to 2% by weight or more. The stabilization reagent is usually in the form of a buffer containing one or more of the stabilization reagents. Suitable buffers may be any convenient buffer, generally a substantially dilute buffer, which may include phosphate, saline, tris, MOPS, borate, carbonate, or the like. Usually, the buffered solution will be at a pH in the range of about 4 to 9. The buffer concentration is generally from about 10 to 50 mM, preferably, about 15 to 25 mM.

The processing reagents may also include one or more reagents for preserving the sample applied to the device such as to prevent bacterial, fungal and other contamination, e.g., bactericides, antibiotics, fungicides and the like. Such reagents include, for example, sucrose, polyvinyl alcohol, polyvinyl pyrrolidone, dextran, sodium azide, gentamicin, Proclin 300® (Supelco, Bellefonte, Pa.) and so forth. The amount of the preservation reagents employed is about 1 to 20 weight percent, more usually from about 2 to 10 weight percent, and the reagent is applied in a manner similar to that described above for the stabilization reagent.

The processing reagents may include one or more reagents for releasing an analyte from binding proteins and the like that might be present in the sample. Such reagents depend on the nature of the analyte and include, for example, sodium hydroxide, tetrachlorothyronine salicylate, 8-amino-1-naphthalenesulfonic acid, 2-hydroxy-4-methoxybenzophenone-5-sulfonic acid, etc. (see EPA 0 133 464), Nonidet P 40® (NP40, from Fluka Chemie AG, Switzerland), Tween 20 and the like. The amount of the analyte-releasing reagent employed is about 0.01 to 2% by weight and the reagent is applied in a manner similar to that described above for the stabilization reagent.

As mentioned above, the sample may be analyzed by any convenient method. Assays include, by way of illustration and not limitation, agglutination assays, precipitation assays, nephelometric assays, turbidimetric assays, immunoassays, coagulation assays, and so forth. The assays may involve members of a specific binding pair such as antigens, antibodies, receptors, and so forth. Such assays include immunoassays, receptor binding assays, coagulation assays, agglutination assays and the like. Detection of an assay result depends on the signal producing system chosen, example of which are set forth above. For example, where the label is a fluorescent label, signal is detected with a fluorometer, and so forth. For enzyme labels, the signal is often detected spectrophotometrically. Exemplary of assays employing enzyme labels are the EMIT® assay described in U.S. Pat. No. 3,817,837, the disclosure of which is incorporated herein by reference, the CEDIA assay, and so forth.

Figure 7:
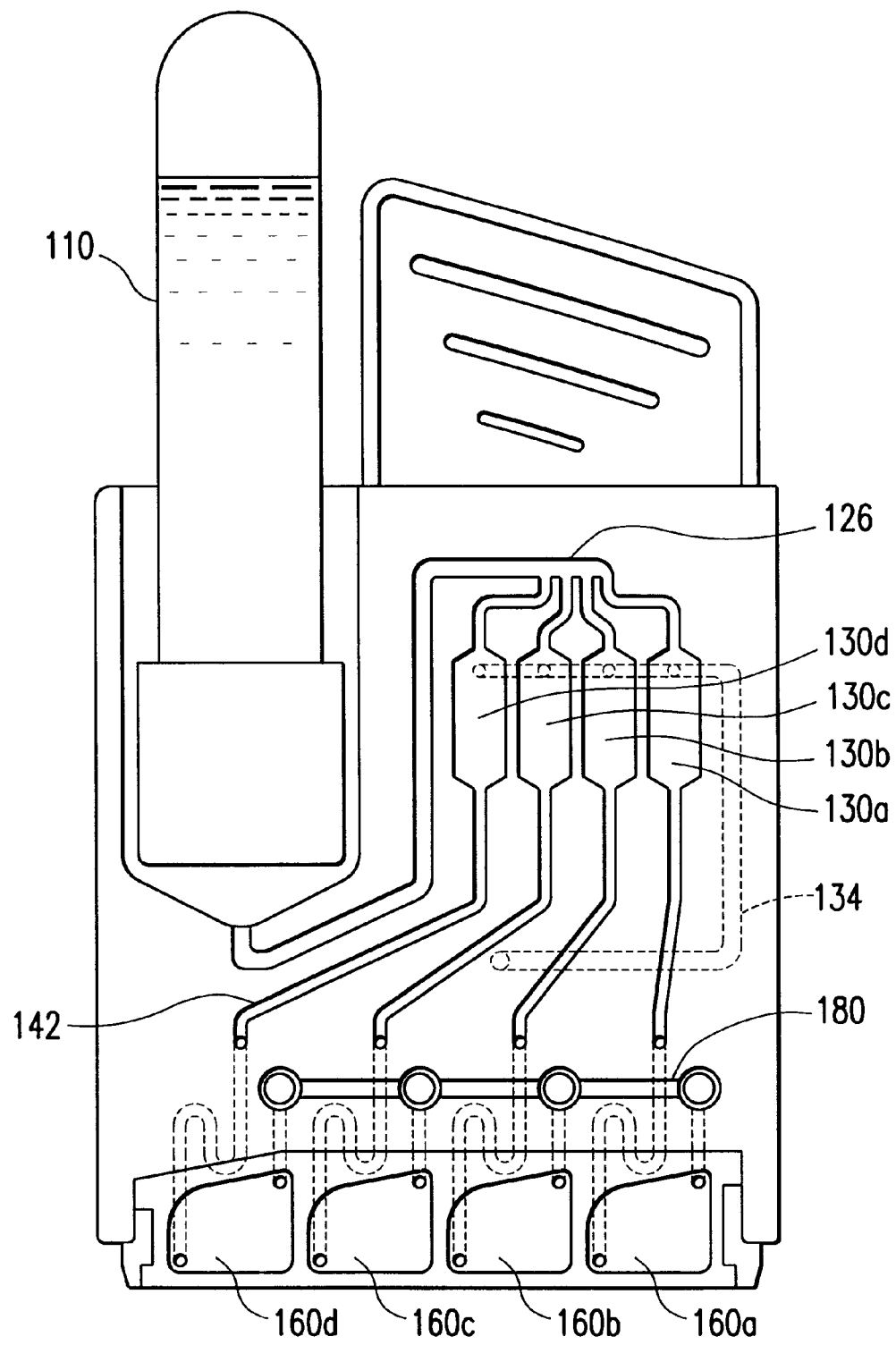
FIG. 7 is a diagrammatic plan view of an alternate embodiment of a device according to the subject invention.

While the embodiments of FIGS. 1 and 5 have been illustrated having four and three second chambers, respectively, there is no inherent limitation upon the number of chambers, which usually will be between one and four. In addition, there may be more than one first chamber (see FIG. 7 depicting first chambers 130a, 130b, 130c and 130d) usually connected in series in fluid communication through channels or capillaries in a manner similar to that described for the first and second chambers. Generally, the last of the first chambers is in direct fluid communication with the first manifold. Likewise, the illustrated embodiments are equipped with magnetic mixing means, which may be substituted as desired with alternative motive means. It is contemplated that the observation of the sample in the assessment chamber will be by optical means, principally via fluorescence or infrared absorption.

Figure 6:
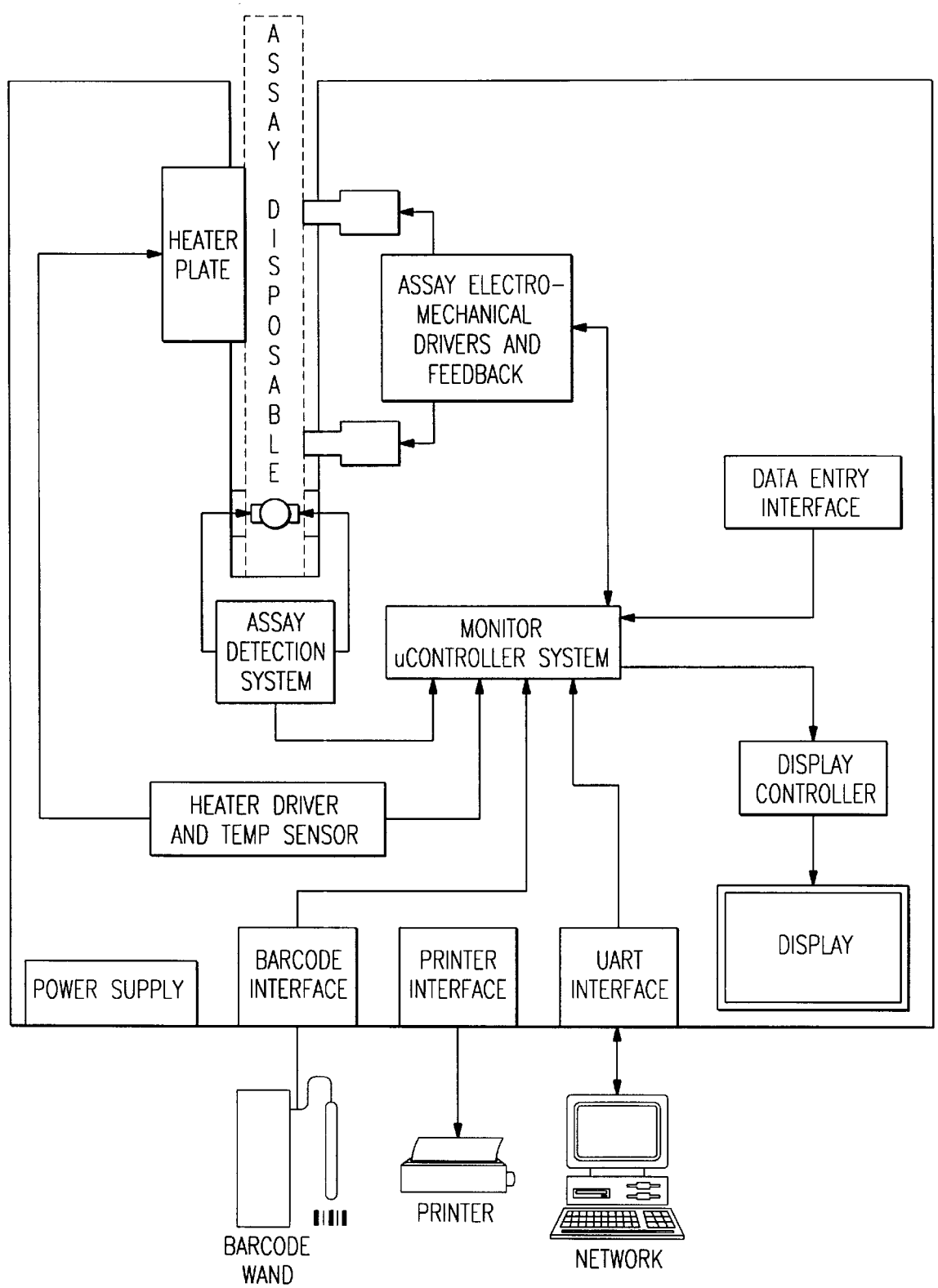
FIG. 6 is a schematic diagram of one embodiment of an instrument that may be employed in conjunction with a device in accordance with the present invention.

An example, by way of illustration and not limitation, of an instrument into which the present device may be employed is depicted in FIG. 6. The instrument includes a turbidimetric-based optical detection system that measures aggregation as an increase in light transmittance. Due to the ratio of bead size to the measurement wavelength, the light scattering is primarily forward (Mie) scatter. As a result, the chambers of the present device are illuminated by a narrow bandwidth emitter with detectors, mounted in direct opposition, to collect the in-coming light. The optical detector converts the light into an electrical current that is input into a transimpedance amplifier and converted to a voltage, which is the measured signal. This instrument is AC powered and is based on an embedded PC architecture. The instrument controls the assay sequencing, establishes and maintains the assay temperature, controls the reagent-sample mixing for the required duration, determines the result, displays result and status information to the user, and performs self-diagnostics. The instrument supports bar code data entry, printing of teat results to an external printer, and an RS-485 interface to interconnect to a laboratory network. The instrument has four independent optical detection channels comprised of narrow band emitters and high gain broadband detectors. Each detector output is A/.D converted at a rate of up to 16 Hz. The assay mixing is controlled by a programmable clock-driven solenoid that provides uniform mixing across all four channels. The temperature of the sample is controlled by a closed-loop feedback design utilizing a precision thermistor and a resistive heater element.

The following description of a platelet function assay utilizing the device of the present invention is provided by way of illustration and not limitation. As mentioned above, the present device has broad application to the processing of many different types of samples without intervening opening of sample containers. An example of a platelet function assay using the device of this invention is similar to the optical platelet aggregation assay of Coller, supra, involving the use of fibrinogen coated microparticles and activating agents. As in optical aggregation, the activated platelets complex with soluble fibrinogen, fibrinogen already bound to the surface of another platelet and fibrinogen coated or bound to the microparticles. As a consequence of the latter, the microparticles coagglutinate with the platelets, forming aggregates of sufficient size so as to be detectable. By varying the type and concentration of activating agent, results substantially equivalent to the platelet aggregometer can be obtained.

In the embodiment of Coller, supra, a 70 ml sample of blood plus anticoagulant is added to a borosilicate tube containing a buffer with 0.05 mM calcium chloride, a blue. bead suspension (20 ml fibrinogen coated beads, 3 mm), and an activating peptide [5 10 ml (iso S)FLLRN NH2, 2 mM final concentration]. After the tube is capped and mixed, the blood is rocked on an end to-end tube mixer and viewed for the presence or absence of bead agglutination. The agglutinated beads are readily seen in the stream of blood as the tube is tilted back and forth, and the extent of agglutination is rated from O+ (no agglutination) to 4+ (extensive agglutination). The assay conditions were designed to yield an end point at 120 seconds in order to satisfy the practical needs for a rapid determination desired in a clinical setting. This method, while entirely satisfactory for its intended use, is however subjective and therefore operator dependent due to the method of assessing and reporting the results. Further, it is desirable to have the ability to generate a permanent, quantified record of various platelet functions.

Assays using turbidimetric methods are usually conducted by first minimizing the concentration of red blood cells (RBC's). This is necessary because RBC's constitute about 45% of the volume of whole blood, and therefore, their absorption and scattering characteristics have a significant impact on transmitted light. Two common methods of reducing the effects of red blood cells on turbidimetric measurements are 1) lysis of the red blood cells and dilution of the resulting solution and 2) mechanical separation of the red blood cells from the sample by centrifugation or filtration through a porous membrane. Certain assays, however, depend upon the integrity of the whole blood to achieve an accurate measurement. For example, with an assay intended to measure platelet aggregation, lysing of RBC's is not acceptable since the lysed RBC's release ADP, a potent platelet activator. Similarly, the use of a porous membrane to filter the RBC's can result in loss of platelets, which adversely affects the measurement of platelet aggregation. Filtering RBC's may also cause hemolysis, again releasing the potent platelet activator ADP. Two problems must be overcome to perform an accurate turbidimetric assay of analyte concentration or functional behavior in whole blood with intact RBC's. First, the method must compensate for the error in optical density readings due to the concurrent change in the oxygenation state of the RBC's in the whole blood sample. Second, the agglutination media (e.g., beads) must have high light absorption characteristics in comparison to RBC's at the measurement wavelength such that agglutination of the light absorbing media results in a detectable change in optical density.

The present invention addresses these problems via the provision of a system consisting of a stand alone monitor and disposable test cartridge based on microbead agglutination technology. The system does not require platelet isolation. The assay requires only a small amount of whole blood and provides quantitative results within a few minutes after blood is drawn.

The assay is based on the principle that fibrinogen coated microparticles exhibit a visible agglutination reaction in whole blood in the presence of activated platelets with normal GPIIb/IIIa receptors. Blockade of the GPIIb/IIIa sites by c7E3 antibody or other agents can be detected by inhibition of microbead agglutination. The assay, unlike other activated coagulation assays, is only minimally influenced by the anticoagulant effect of heparin and is believed to primarily reflect GPIIb/IIIa status, unless there is severe thrombocytopenia or serious qualitative platelet dysfunction. The presence of normal plasma levels of fibrinogen (2–4 mg/ml) also does not greatly influence the assay because of preferential interaction of the platelets with the immobilized fibrinogen. In practice, the assay requires the presence of an agglutination medium, preferably GPIIb/IIIa receptor land coated microparticles, a platelet activating agent, means for observing the aggregation of the microparticles, and means for recording, compiling, and displaying the results. Each of these is discussed more fully below.

Receptor Ligands:

A GPIIb/IIIa receptor ligand is a small organic molecule, polypeptide, protein, monoclonal antibody or nucleic acid that binds, complexes or interacts with GPIIb/IIIa receptors on the platelet surface. Platelet mediated aggregation of the microparticles results when the GPIIb/IIIa receptors on the surface of platelets bind, complex or otherwise interact with the GPIIb/IIIa receptor ligands on the particles or beads. Typical GPIIb/IIIa ligands include fibrinogen, monoclonal antibody 10E5 (Coller, et al., J. Clin. Invest. 72:325 (1983)), monoclonal antibody c7E3 (The EPIC Investigators, N.E. Journal of Med., 330:956 (1994)), von Willebrand factor, fibronectin, vitronectin and other ligands that have an arginine glycine-aspartic acid (RGD) sequence or other peptides or peptidomimetics that mimic this sequence (Cook, et al., Drugs of the Future 19:135 (1994)). RGD functionally equivalent ligands include gamma chain peptides, peptidomimetics and cyclic peptides with activity about the same as an RGD ligand surface through a suitable spacer. Examples of suitable ligands are disclosed in Beer, et al., Blood 79:117 (1992), the contents of which are incorporated herein by reference. Suitable GPIIb/IIIa receptor ligands include the peptide (glycine)n arginine glycine aspartic acid, wherein n is an integer from 220. The polyglycine portion of the ligand serves as a spacer and is covalently bound to the surface of the polymeric bead via the N terminal amino group. While the RGD sequence may participate in the binding of platelets, a gamma chain sequence forming a molecular mimic of the RGD sequence may be more important in the binding of fibrinogen to platelets (Coller, Platelet Morphology, Biochemistry, and Function, 1175). Optionally, an additional amino acid or oligopeptide that does not significantly interfere with the binding of arginine glycine aspartic acid to the GPIIb/IIIa receptor may be bound to the C terminus of aspartic acid by means of a peptide bond. In one embodiment, the GPIIb/IIIa receptor ligand comprises (Glycine)9–11-arginine glycine aspartic acid phenylalanine. Alternatively, the spacer portion of the ligand can comprise any moiety which causes the arginine glycine aspartic acid sequence to extend out from the surface of the microparticle sufficiently to allow binding between the ligand and GPIIb/IIIa receptors on the surface of platelets and does not significantly interfere with the ability of arginine glycine aspartic acid to bind with GPIIb/IIIa. Examples of suitable moieties include alkyl groups and polyglycol groups.

Activating Agents:

The thrombin receptor is a transmembrane protein that is present in platelets (Vu, et al., Cell 64:1057 (1992)). A thrombin receptor activator, as defined herein, is a peptide, protein, antibody or small organic molecule that induces platelet activation via the thrombin receptor, i.e., which increases the rate of agglutination when platelets whose GPIIb/IIIa receptors are not blocked when the platelets are combined with a GPIIb/IIIa receptor ligand bound to solid surfaces. A suitable peptide is any peptide of appropriate sequence and size to activate platelets, as described above. The peptide can comprise thrombin, or a portion thereof, such that the amino acid sequence of the peptide or peptide mimic result in activation of the platelets. Vu, et al., identified the amino acid sequence of the thrombin receptor and proposed a mechanism of thrombin receptor activation. Thrombin cleaves the thrombin receptor protein, releasing a short receptor fragment and leaving a new amino terminal peptide on the platelet surface. The new amino terminal peptide activates the receptor by functioning as a tethered ligand that interacts with another region of the receptor to induce activation signals. A fourteen amino acid peptide (T14) corresponding to the new N terminus of the cleaved receptor protein is capable of aggregating platelets directly without prior thrombin cleavage (Vu, et al). However, the entire peptide is not required for activity because an eleven amino acid peptide (T11) lacking the three C terminal amino acids of T14 is twice as potent as T14 (see Coller, et al., Biochemistry 31:11713 (1992), the contents of which are hereby incorporated by reference). A peptide comprising the first five or six amino acids has also been shown to be active. (Vassallo, et al., J. Biol. Chem. 267:6081 (1992), Hui, et al., Biochem. Biophys. Res Commun. 184:790 (1992), Sabo, et al., Biochem. Biophys. Res. Commun. 188:604 (1992) and Scarborough, et al., J. Biol. Chem. 267:13146 (1992).

The N-terminal serine group of the thrombin receptor activating peptides is essential to their ability to induce platelet aggregation,. This conclusion is based on the observation that acetylation of the N terminal serine of T11 results in loss of aggregating ability. In addition, T11 and T14 lose their ability to accelerate aggregation when incubated in plasma because the plasma component aminopeptidase M cleaves the N terminal amino acid. The presence of aminopeptidase M in whole blood can result in variability in the amount of time required for agglutination of the beads in the assay. Acetylation of the N terminus of the thrombin receptor peptide ligand is the traditional method for producing a peptide that resists cleavage by aminopeptidase M, but acetylation of this ligand eliminates receptor activator activity.

The variability in the time required for agglutination can be avoided by carrying out the assay under conditions wherein the cleavage of the N terminal serine of the thrombin receptor activating peptide is suppressed. This can be accomplished by employing a thrombin receptor activating peptide (TRAP) that is resistant to degradation by aminopeptidase M. The rate of microbead agglutination is more rapid and reproducible if the platelets are activated. A variety of TRAPs are disclosed and claimed in Coller and Prestwich, U.S. Pat. No. 5,455,228, the relevant disclosure of which is incorporated herein by reference. These peptide derivatives are resistant to cleavage and inactivation by plasma aminopeptidase M, thus eliminating a potential source of variability. The level of GPIIb/IIIa receptor activation, and therefore the fibrinogen binding capacity of the platelets, is dependent upon the amount of added activating peptide. A preferred thrombin receptor activating peptide that is resistant to degradation by aminopeptidase M is racemic isoSer-Phe-Leu-Leu-Arg-Asn. This peptide is hereinafter referred to as T6'. See Coller and Prestwich, U.S. Pat. No. 5,455,228, and Coller, et al., J. Biol. Chem. 268:20741 (1993)), the contents of which are incorporated into this application by reference). Other suitable thrombin receptor activating peptides that are resistant to aminopeptidase M include peptides comprising an N terminus having the amino acid sequence of T6', such that the peptide is resistant to aminopeptidase M degradation and retains sufficient platelet activating activity, as described above. Alternatively, the variability can be avoided by including an inhibitor of aminopeptidase M in the assay. A suitable inhibitor of aminopeptidase M is amastatin, which has been shown to enhance platelet aggregation in the presence of aminopeptidase M (Coller, et al., Biochemistry 31:11713 (1992)).

Other platelet activators can be used in place of the thrombin receptor activating peptides described above. For example, adenosine diphosphate (ADP), collagen, ristocetin, botrocetin, epinephrine, arachidonic acid and its metabolites including thromboxane A2, platelet activating factor, plasmin, serotonin, vasopressin, tissue plasminogen activator, streptokinase and immune complexes can be added, alone or in combination with other platelet activators, to increase the rate of agglutination of the beads in the assay of the present invention. Additionally, application of high levels of shear stress, and artificial surfaces such as those used clinically for prosthetic materials can also activate platelets (Coller, Platelet Morphology, Biochemistry, and Function, 1185)

Agglutination Media:

The agglutination media may be any suitable solid surface bearing a receptor ligand. Preferably the surface is a small polymeric bead or microparticle to which a GPIIb/IIIa receptor ligand is covalently bound or absorbed. The polymeric microparticles can be virtually any shape, but are generally spherical with uniform diameters ranging from about 0.1 mm to about 50 mm in diameter. Preferred diameters are from about 1 mm to about 10 mm in diameter, most preferably about 6 mm. The composition of the particle may be any convenient composition, such as bioglas, organic polymers, e.g. polyacrylonitrile, polystyrene, polycarbonate, polymethacrylate, combinations thereof, or the like, or other material which absorbs in the infrared or can be made to do so with infrared absorbing dyes. For the most part the particle composition without the dye will not absorb significantly in the infrared region of interest, usually absorbing less than about 25% of the total light absorbed in that region compared to the particle doped with the infrared absorbing dye. Also, there will be many regions in the visual region in which the particle composition will be substantially transparent, as distinguished from carbon or colloid particles which do not transmit light over the visual and infrared region. Usually, at least 50 weight %, preferably at least about 75 weight %, will be of a size or diameter within the range indicated. The particles may be modified in a variety of ways. The particles may be chemically activated by having functional groups present on the surface of the particles, or be coated with a compound, e.g. protein, which may serve to substantially irreversibly (under the conditions of the processing and assay) bind to the dye. The coating compound may be the binding component, which will be involved in the aggregation of the particles, or other compound, usually being a protein. Alternatively, depending on the nature of the particles, the particles may not have chemically active groups, but rather provide binding by adsorption. In addition, infrared absorbing dyes which are stable under the conditions of formation of the particles, e.g. extrusion, may be mixed with the polymer prior to particle formation and the particle formed with the dye distributed throughout the particle.

The particles are loaded with a dye which absorbs in the infrared. Various dyes have been reported as useful in this absorption range. See, for example, Fabian, et al., Chem. Rev. (1992) 92:1197 1226. These dyes include bacteriochlorin, bacteriochlorophytin, meropolymethine dyes, benzoannulenes, vinylogous porphyrins, polymethine dyes, cyanines and merocyanines, and the like. The particular dye which is selected is one of convenience, availability, stability, compatibility with the particle, and the like. Specific dyes of interest include dyes of the class of phthalocyanines, napthalocyanines, metaled napthalocyanine dyes, and modified natural bacterochlorines. Specific example dyes include IR 140, 1,1' Diethyl 4,4' dicarbocyanine iodide, 1,1' Diethyl 2,2' quinotncarbocyanine iodide, Vanadyl,10,17,24 tetra tert butyl 1, 8, 15, 22, 25 tetrakis (dimethylamino) 29H,31H phthalocyanine, [RA800 (from Exciton), ProJet 830NP (from Zeneca). These dyes may be incorporated directly into the particle itself, through polymerization or passive adsorption. Alternatively, the dyes may be linked to the bead in combination with the binding component, such that they do not leach from the surface. The dyes will adsorb light in the range of about 750 900 nm, particularly in the range of about 750 850 nm. For samples with high levels of red blood cells, the light will be at about 800 nm±10 nm, which is the isobestic point for oxyhemoglobin and reduced hemoglobin. The amount of the dye employed with the particles will vary with the extinction coefficient of the dye in the light range of interest, the required sensitivity of the assay, the size of the particles, the mode of binding of the dye to the particles, compatibility of the dye with the particle matrix, and the like. Usually, loading will be in the range of about 1 to 20 weight percent, more usually 5 to 15 weight percent.

For example, the polymeric microparticle may be polyacrylonitrile beads with N hydroxysuccinimide ester groups on their surface (e.g., Matrex 102 beads from Amicon Corporation) (Coller, Blood, 55:169 (1980)). The N hydroxysuccinimide ester groups allow coupling of the N terminus of a peptide, protein or monoclonal antibody to the surface of the bead. Alternatively, the microparticle can be carboxylated polystyrene beads (Polysciences Inc.). The surface carboxyl groups of this bead can be coupled to the N terminus of the protein, peptide or monoclonal antibody by means of a carbodiimide coupling. The beads are preferably colored to render the results of the agglutination reaction easier to interpret. In a preferred embodiment, the beads are adapted to absorb light in the infrared region.

To eliminate effects of red blood cell oxygenation, an IR source of wavelength of about 800 nm is preferred since oxyhemoglobin and deoxyhemoglobin have the same optical absorption coefficient at 805 nm. Assay dependence upon the variable state of red blood cell oxygenation is thereby eliminated. Further, the hemoglobin isobestic point at 805 nm has the lowest absorption coefficient between 300 nm and 1000 nm. This results in the widest possible differential between light absorption by the red blood cells versus that by the agglutination medium (beads).

The agglutination medium is selected to have high absorption at ~800 nm. The ratio between the agglutination medium absorption coefficient and whole blood absorption coefficient should preferably be greater than about 4:1 at 800 nm. The absorption ratio for a particular assay is a function of both the absorption coefficient of the agglutination medium and the concentration of the agglutination medium in the assay sample.

The IR absorbing particles preferably have the following properties: absorption peak around 800 to 810 nm; reasonably broad half widths (>75 nm) around the absorption peak; little or no fluorescence (high fluorescence requires the use of a high pass optical filter), and a molar extinction coefficient of about 30,000.

Four categories of IR absorbing particles are useful in the assay: latex particles dyed with IR dyes, D1 dye sole, carbon black particles, and liposomes with entrapped IR absorbers. The particles are preferably spherical beads about 6 mm in diameter.

Generally, an hydrophobic IR dye soluble in organic solvents is preferred. Latex particles are dyed with the IR dye according to established methods using dyes which absorb in the visible range at about 800 nm (see Lee Bangs, Uniform Latex Particles). Latex offers the advantage of size uniformity. Water insoluble dyes may be induced to form colloids (sols, sub micron or larger particles) when a solution of the dye in a water miscible solvent is added to water. Carbon black absorbs well in the IR region of the spectrum and can be dispersed in aqueous solutions by sonication. Liposomes with entrapped IR absorbers, e.g., a water soluble IR dye, can be tailored to the desired sizes and fibrinogen bound to the surface via an anchor compound, such as palmitoyl chloride.

Preferably, the concentration of beads is adjusted so that the platelet/bead ratio is from about 1.9 to about 2.8. A GPIIb/IIIa ligand may be covalently or ionically coupled to the bead, or the ligand may be simply coated on the bead. In one embodiment the ligand bearing beads are lyophilized. A representative formulation for lyophilization is about 10 mg/ml beads, 75 mg/ml fibrinogen, and 200 mg/ml bovine serum albumin.

The time for fluxing may be varied widely, usually being at least about 1 sec. and not more than about 5 min., usually not more than about 2 min., and preferably for about 5 sec. to 1 min.

The particular manner of agitation is not critical, so long as it provides for thorough mixing, without preventing the formation of aggregates. If desired, mild agitation may be maintained during the course of the assay, again insuring that there is homogenous distribution of the particles and any other particulate matter, while insuring that aggregation is not impeded.

The temperature for the assay may be varied widely, depending upon the nature of the component of interest. Conveniently, ambient temperatures may be employed, although elevated temperatures which can be controlled and maintained are preferred. Where nucleic acids are involved, the temperature may be elevated, so as to enhance the degree of stringency of hybridization. Thus, the temperature may vary from about 15 90° C., where with other than nucleic acids, the temperature will generally vary from about 25 40° C. Usually, with nucleic acids the temperature will generally be in the range from about 20 90° C., more usually in the range of about 30 85° C.

The time for the assay will depend upon the manner in which the measurement is taken. Where zero time is carefully controlled, one may take one or two measurements at different time intervals to determine the absolute infrared transmission at the time intervals or determine the rate of formation of the aggregation. Alternatively, one may take a plurality of measurements over the time course of the assay and analyze the slope beginning at a fixed time from the time of mixing. The data may be analyzed by any convenient means, particularly using an algorithm which can manipulate the data in relation to calibrators and/or controls. The total time of the readings from the zero time (time of mixing), may range from about 10 sec. to 5 min., more usually about 30 sec. to 5 min., and preferably about 30 sec. to 2 min.

Usually, the result will be compared to a calibrator, which may be performed concomitantly or have been performed previously or may be provided as a standard curve. The calibrators will vary depending upon the nature of the component of interest. Samples having known amounts of the component of interest may be prepared and performed in the assay and the results charted so as to be able to translate the measurement obtained with the sample to the standard. In some instances controls will be used, where the base value may vary depending on the source of the sample. The particular control will be associated with the sample and the component of interest.

Where platelet aggregation is to be measured, because of interest in the platelet status of an individual, which may be the natural status or the status resulting from administration of a drug, the sample will be in effect whole blood, which has been subjected to less than about 50%, preferably less than about 20% dilution.

The whole blood is drawn desirably in the substantial absence of air. Conveniently, a Vacutainer is employed for capturing and holding the blood sample. The Vacutainer desirably includes a small volume of a solution of sodium citrate generally in the range of about 35% sodium citrate having a volume in the range of about 0.05 0.5 ml. The blood sample should be obtained from an extremity free of peripheral venous infusions. Conveniently, the needle should be at least about 21 gauge.

The first tube which is withdrawn is discarded, the second tube or subsequent tubes being used. Mild agitation by simply gently inverting the Vacutainer is employed to insure the mixture of the anticoagulant with the sample. The sample in each container may range from about 110 ml, more usually from about 18 ml, conveniently from about 15 ml. The sample should not be stored for an unduly long period, generally storage before the assay should not exceed 1 hour.

The container containing the whole blood is then secured to a device of the present invention as described above, an example of which is shown in FIG. 1. The second chambers contain the particles that have been coated with fibrinogen as well as various agents that serve to activate the platelets. Illustrative agents include iso TRAP (See U.S. Pat. No. 5,455,228), TRAP, ADP, collagen, thrombin, ristocetin, or any combination thereof. Any convenient activator may be employed. Iso TRAP is employed at a concentration in the range of about 1 to 5, preferably about 2 Tmol/L. The activating agent may be incorporated with the bead reagent to which the blood sample is added. The beads and other reagents may be dry, so as to not dilute the sample, although in some instances a small amount of liquid may be present, desirably less than about 25% of the volume of the sample.

The particles are conveniently polystyrene particles of a size in the range of about 2 to 8 microns, which have been coated with fibrinogen by passive adsorption or by covalent linkage in accordance with conventional ways. Generally, the weight of fibrinogen to the weight of particles volt be in the range of about 1:1000 to 1:10.

The amount of beads should provide a ratio between the agglutination media absorption coefficient and whole blood absorption coefficient of greater than about 4:1 at 800 nm, generally, not more than about 10:1 at 800 nm. The optimal absorption ratio may be achieved by configuring both the light absorbing characteristics of the agglutination media and the concentration of the agglutination media in the assay sample.

As mentioned above, the sample container is secured to the present device. The sample container is inverted and inserted into the well of the device of FIG. 1 whereupon the needle therein pierces the septum of the sample container. The device is then inserted into an instrument that provides both a pneumatic circuit and a reading function as mentioned above.

Sample is moved into the first chamber as described above by adjusting the pressure in the device using the pneumatic circuit. Generally, the volume of the sample transferred into the first chamber is about 0.1 to 2 ml. The blood in the first chamber is incubated at 37° C. for 2 minutes. Then, the blood is moved into the second chambers as described above where it mixes with the particles and other reagents.

The mixture of citrates, whole blood, particles and activating agent is gently agitated by causing the mixing ball contained in the second chambers to magnetically activate. Mixing insures homogeneity and the mild agitation is continued so as to maintain homogeneity without impeding aggregation formation. The temperature for the medium will be maintained at a constant temperature. After a short time, generally under 30 sec., usually under about 10 sec., readings are begun by illuminating the sample with light at about 800 nm. The total time for the readings will generally be under about 5 min., usually 3 min. When one is determining the rate of change to determine the change in slope with time, the number of data points per second may range from about 0.01 to 100, more usually from about 1 to 50. Thus, one reagent may then be combined with the particles coated with fibrinogen in the same manner as the sample. If desired, the buffered medium may be augmented with blood constituents, such as red blood cells, serum albumin, immunoglobulins, or other significant constituent of blood, which does not participate in the aggregation of the particles.. A convenient buffer medium is HEPES sodium chloride buffer comprising from 1–5 mg/ml protein, e.g., BSA.

After the sample has been combined with the reagents, desirably it will be heated to a temperature above room temperature, but below interference with the assay, so as to insure that the temperature can be controlled without adversely affecting the assay result. Desirably, the temperature should be at least 25°, preferably in the range of 30–40° C., more preferably about 37° C.

Another aspect of the present invention is a kit for processing a sample. The kit comprises in packaged combination a device as described above. The kit may also include, in predetermined amounts, reagents for processing a sample other than those included in the device. The kit may also include a sample collection container. Where the device is for conducting an assay, reagents for conducting an assay for an analyte in a sample may be included. The relative amounts of reagents may be varied widely to provide for concentrations in solution of the reagents which substantially optimize the sensitivity of an assay. Where appropriate, the present device and reagents can be placed in an air-tight package in order to maintain the activity of any reagents. The package may be, for example, a bag, pouch, or the like fabricated from a material that is substantially non-permeable to moisture. Such materials include, by way of example and not limitation, plastic, aluminum foil, and the like. For blood samples the kit may also include an article for piercing a person's skin, disinfectant or sterilizing pads and so forth. It will be evident that the nature of additional articles to be included in the kit with the device of the present invention are dependent, among others, on the type of sample being collected. These articles will be known to the skilled person.

For platelet function assays, kits can be provided comprising some or all of the reagents which find use in such assay. The kit will have the particles for use with the component of interest. In addition, neutralizing immunoglobulins may be provided for removing inhibitor in a sample to serve as a control. Calibrators may be provided providing particles with the appropriate binding component mixed with any other reagents associated with the assay and, if desired, a source of the component of interest, either in measured amounts or in bulk. For platelet aggregation, a combination of thrombin and uncoated particles may be supplied. Also, of convenience, would be Vacutainers comprising 0.11 ml of 15M anticoagulant, e.g. sodium citrate. Of particular Interest for the kit is a container containing one or more of the appropriate reagents in order to reduce the manipulative steps for the assay. For example, a container, such as a cuvette, may be provided containing the particles and, as appropriate, other reagents for the assay.

EXAMPLES

The following examples are offered by way of illustration and not by way of limitation. Parts and percentages are by weight unless otherwise indicated. Temperatures are in degrees Centigrade (°C.) unless indicated otherwise. The following preparations and examples illustrate the invention but are not intended to limit its scope.

Example 1

Preparation of IR particles coated with hFg.

Water (8.72 mL) and 1M sodium phosphate at pH7.2 (0.2 mL) were first fluxed in a 1 SOL conical tube. Purified hFg (82.5 ml at 40 mg/mL, Enzyme Research Laboratories) was then added and gently mixed. This was followed by a bolus addition of 1 mL of a 10% particle suspension of beads (Matrex, 100 mg solids/mL) and quickly mixed. The mix was incubated on a rocker at room temperature for about 2 hours, after which it was centrifuged to remove the supernatant and washed untie the storage buffer twice. The final particle concentration was 1 to 1.5% in storage buffer.

Example 2

Preparation of dye coated particles.

IR140 (a cationic IR dye from Lambdochrome Laser Dyes) was dissolved in minimal volume of methylene chloride to make a solution about 5 mg/mL in IR140.2 Propanol (38 parts) was then added to 9 parts of the above solution, followed by 53 parts of 20 mM sodium phosphate at pH7.5 to make up the final dye solution. Polystyrene latex beads with carboxyl functional groups, passively coated with human fibrinogen (hFg) as taught in Example 1, were washed, pelleted and finally mixed with the above dye solution (1 mL per 10 mg of latex) at room temperature for 5 minutes. The mix was then diluted with 10 volumes of 20 mM sodium phosphate at pH7.5 containing 1 mg/mL BSA (storage buffer) prior to centrifugation to minimize aggregation. The resulting pellets were then washed with the storage buffer to yield the final dyed beads. Further dye loading using the process of Example 2 may be accomplished. If the application is such that the desired substance on the bead is not hFg, agents such as SMCC can be used to modify hFg for later attachment of sulfhydryl containing or sulfhydryl modified substances.

It is evident from the above results that a simple device is provided. The user is only required to place a sample container, into which a sample has been collected, in the present device to secure it to an input port. The present device is then placed into an apparatus for assisting in introducing the sample into the device and assaying the sample. The device is easily manipulated without risk to the operator and without risk of compromising the sample. The device provides for precise measurement of the sample into chambers wherein the sample is analyzed and quantitative results are obtained.

All publications and patent applications cited in this specification are wherein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for receiving and processing a sample, said device comprising:
   (a) a sample receiving element comprising an input port that provides for direct sealing connection and establishment of fluid communication with a sample container such that sample in said container is capable of introduction into said device,
   (b) a first chamber in fluid communication with said input port,
   (c) one or more second chambers each respectively in fluid communication with said first chamber, said second chambers containing one or more reagents for processing said sample,
   (d) a first port for connecting said device with a pressure varying apparatus for alternately increasing and decreasing pressure in the device,
   (e) a second port for venting said device, and
   (f) means for permitting air to escape from said one or more second chambers and for sealing said one or more second chambers when a predetermined amount of said sample fills said one or more second chambers.

2. The device of claim 1 which comprises a detector for each of said one or more second chambers for detecting when said second chambers become filled with said sample.

3. The device of claim 1 wherein said sample receiving element is part of a housing adapted to mate with and hold said sample container.

4. The device of claim 1 wherein said one or more reagents for processing said sample are reagents for conducting an assay.

5. The device of claim 1 comprising a plurality of first chambers.

6. A device for receiving and assaying a sample, said device comprising:
   (a) an input port comprising a needle for piercing a sample container and allowing introduction of a sample suspected of containing an analyte directly into said device,
   (b) a first chamber in fluid communication with said input port by means of a first channel connecting said input port and said first chamber,
   (c) a manifold in fluid communication with said first chamber,
   (d) one or more second chambers each respectively in fluid communication with said manifold by means of a second channel between said manifold and said respective second chamber, said one or more second chambers containing one or more reagents for conducting an assay,
   (e) a first port for connecting said device with a pressure varying apparatus for alternately increasing and decreasing pressure in the device,
   (f) a second port for venting said device,
   (g) a vent plug for each of said one or more second chambers for permitting air to vent from said one or more second chambers and sealing said one or more second chambers when said sample reaches said vent plug.

7. The device of claim 6 which comprises a detector for each of said one or more second chambers for detecting when said one or more second chambers become filled.

8. The device of claim 6 which comprises a detector for monitoring premature movement of said sample from said first chamber to said one or more second chambers.

9. The device of claim 6 wherein said input port is part of a housing adapted to mate with and hold said sample container.

10. The device of claim 6 wherein said one or more reagents for conducting an assay are reagents for conducting an assay for the presence or amount of an analyte in said sample.

11. The device of claim 6 wherein said one or more reagents for conducting an assay are reagents for conducting a platelet function assay on a blood sample.

12. The device of claim 6 wherein said port for connecting said device to a pressure varying apparatus is at the end of a third channel in communication with said first chamber.

13. The device of claim 6 wherein said first port is in communication with a pressure varying apparatus.

14. The device of claim 13 wherein said pressure varying apparatus is selected from the group consisting of diaphragm pumps and reversible pumps.

15. The device of claim 6 wherein said vent port is connected to a valve for controlling the venting of gas from said device.

16. The device of claim 6 comprising a separation means in fluid communication with said input port.

17. The device of claim 6 wherein said first chamber has one or more reagents for stabilizing and/or preserving said sample and/or an analyte contained therein.

18. The device of claim 6 wherein said input port also comprises an indicator for indicating whether sample has been contacted with said input port.

19. The device of claim 6 comprising a plurality of first chambers connected in series.

20. A kit for carrying out an assay on a sample suspected of containing an analyte, said kit comprising in packaged combination:
   (a) the device of claim 6 and
   (b) reagents for conducting an assay for an analyte in said sample.

21. A method of receiving and processing a sample, said method comprising:
   (a) applying a sample to a sample receiving element of a device comprising:
      (i) a sample receiving element comprising an input port that provides for direct sealing connection and establishment of fluid communication with a sample container such that sample in said container is capable of introduction into said device,
      (ii) a first chamber in fluid communication with said input port, (iii) one or more second chambers each respectively in fluid communication with said first chamber, said second chambers containing one or more reagents for processing said sample,
(iv) a first port for connecting said device with a pressure varying apparatus for alternately increasing and decreasing pressure in the device,
(v) a second port for venting said device, and
(vi) means for permitting air to escape from said one or more second chambers and for sealing said one or more second chambers when a predetermined amount of said sample fills said one or more second chambers.

(b) connecting said first port to a pressure varying apparatus,
(c) adjusting pressure to said device to cause said sample to flow from said sample receiving element to said first chamber,
(d) adjusting pressure to said device to cause said sample to flow from said first chamber to said one or more of said second chambers, and
(e) processing said sample.

* * * * *